US010471088B2

(12) United States Patent
Giovannone et al.

(10) Patent No.: US 10,471,088 B2
(45) Date of Patent: *Nov. 12, 2019

(54) SOLID ORAL COMPOSITIONS BASED ON S-ADENOSYL METHIONINE AND/OR NADH AND PROCESS FOR OBTAINING THEM

(71) Applicant: GNOSIS SPA, Milan (IT)

(72) Inventors: Daniele Giovannone, Frosinone (IT); Carlo De Angelis, Fontana Liri (IT)

(73) Assignee: GNOSIS SPA, Milan (IT)

( * ) Notice: Subject to any disclaimer, the term of this patent is extended or adjusted under 35 U.S.C. 154(b) by 425 days.

This patent is subject to a terminal disclaimer.

(21) Appl. No.: 14/718,789

(22) Filed: May 21, 2015

(65) Prior Publication Data

US 2015/0306126 A1 Oct. 29, 2015

Related U.S. Application Data

(63) Continuation of application No. 12/240,002, filed on Sep. 29, 2008, now abandoned, which is a continuation-in-part of application No. PCT/IT2006/000610, filed on Aug. 8, 2006.

(30) Foreign Application Priority Data

Mar. 31, 2006 (IT) .............................. MI2006A0629

(51) Int. Cl.
| | | |
|---|---|---|
| A61K 31/7076 | (2006.01) | |
| A61K 9/46 | (2006.01) | |
| A61K 9/20 | (2006.01) | |
| A61K 9/28 | (2006.01) | |
| A61K 31/52 | (2006.01) | |
| A61K 31/7084 | (2006.01) | |

(52) U.S. Cl.
CPC ........ *A61K 31/7076* (2013.01); *A61K 9/0007* (2013.01); *A61K 9/2009* (2013.01); *A61K 9/2095* (2013.01); *A61K 9/282* (2013.01); *A61K 31/52* (2013.01); *A61K 31/7084* (2013.01)

(58) Field of Classification Search
CPC ................ A61K 31/7076; A61K 31/52; A61K 31/7084; A61K 9/0007; A61K 9/2095; A61K 9/2009; A61K 9/7084
USPC ....................................................... 424/474
See application file for complete search history.

(56) References Cited

U.S. PATENT DOCUMENTS

| | | | |
|---|---|---|---|
| 3,012,943 A | 12/1961 | Morse | |
| 3,330,729 A | 7/1967 | Johnson, Jr. | |
| 3,893,999 A | 7/1975 | Fiecchi | |
| 3,954,726 A | 5/1976 | Fiecchi | |
| 4,057,686 A | 11/1977 | Fiecchi | |
| 4,369,177 A | 1/1983 | Kozaki et al. | |
| 4,394,449 A * | 7/1983 | Modrovich | C12P 1/00 435/12 |
| 4,465,672 A | 8/1984 | Gennari | |
| 4,558,122 A | 12/1985 | Gennari | |
| 4,704,365 A | 11/1987 | Yost | |
| 4,870,059 A | 9/1989 | Mitsuhashi et al. | |
| 6,093,703 A | 7/2000 | La Greca | |
| 6,451,341 B1 | 9/2002 | Slaga et al. | |
| 2002/0010147 A1 | 1/2002 | Berna | |
| 2002/0132780 A1 | 9/2002 | Heisey et al. | |
| 2004/0131805 A1* | 7/2004 | Merical | B32B 7/06 428/34.1 |
| 2004/0209841 A1 | 10/2004 | Oku et al. | |
| 2006/0069059 A1 | 3/2006 | Shaller et al. | |
| 2007/0066578 A1 | 3/2007 | Shimizu | |
| 2017/0312207 A1* | 11/2017 | Saeki | A61K 8/60 |

FOREIGN PATENT DOCUMENTS

| | | |
|---|---|---|
| EP | 0 009 222 | 4/1980 |
| EP | 0 162 323 | 11/1985 |
| JP | 60181095 | 9/1985 |
| JP | 60-255735 | 12/1985 |
| JP | 2091018 | 3/1990 |
| JP | WO2005027932 A1 | 3/2005 |
| WO | 94/25007 | 11/1994 |
| WO | 00/18259 | 4/2000 |
| WO | 01/90130 | 11/2001 |

(Continued)

OTHER PUBLICATIONS

Instituto Della Enciclopedia Italiana, "salificazione," Vocabolario Della Lingua Italiana, 1994, p. 25, Arti Grafiche Ricordi, Milano, Italy.

(Continued)

*Primary Examiner* — Adam C Milligan

(74) *Attorney, Agent, or Firm* — Wenderoth, Lind & Ponack, L.L.P.

(57) ABSTRACT

This invention relates to solid oral compositions based on SAMe and/or NADH or their salts in association with calcium oxide and/or calcium hydroxide and a process for obtaining them.

This invention also relates to a method for stabilising a solid oral composition based on SAMe and/or NADH or their salts, making use of calcium oxide, calcium hydroxide optionally in association with malic acid, glutamic acid, xylitol, calcium sulphate hemihydrate, magnesium oxide and/or mixtures thereof.

This invention also relates to the use of SAMe or its salts in association with calcium oxide and/or calcium hydroxide with the possible further addition of melatonin and/or l-theanine and/or l-tryptophan and/or 5-hydroxytryptophan for the treatment of depressive states.

7 Claims, 2 Drawing Sheets

(56) References Cited

FOREIGN PATENT DOCUMENTS

| WO | 01/93847 | 12/2001 |
|---|---|---|
| WO | 02/089823 | 11/2002 |
| WO | 02/102823 | 12/2002 |
| WO | 03/043608 | 2/2003 |
| WO | WO2005084670 A1 | 9/2005 |
| WO | 2007/004244 | 1/2007 |

OTHER PUBLICATIONS

Instuituto Della Enciclopedia Italiana, "formulato," Vocabolario Della Lingua Italiana, 1987, p. 497, Arti Grafiche Ricordi, Milano, Italy.
International Search Report for PCT/IT2007/000736, dated Aug. 6, 2008.
Written Opinion for PCT/IT2007/000736, dated Aug. 6, 2008.
International Search Report for PCT/IT2006/000610, dated Jan. 24, 2008.
Written Opinion for PCT/IT2006/000610, dated Jan. 24, 2008.
Birkmayer, J. G. D. et al: "Safety of stabilized, orally absorbable, reduced nicotinamide adenine dinucleotide 3 (NADH): A 26-week oral table administration of ENADA/NADH for chronic toxicity study in rats", Drugs Under Experimental and Clinical Research 2002, vol. 28, No. 5.

\* cited by examiner

SOLID ORAL COMPOSITIONS BASED ON S-ADENOSYL METHIONINE AND/OR NADH AND PROCESS FOR OBTAINING THEM

This application is a divisional of U.S. application Ser. No. 12/240,002 filed Sep. 29, 2008, which is a CIP of PCT/IT2006/000610 filed Aug. 8, 2006, which claims priority benefit of Italian application Serial No. MI2006A000629 filed Mar. 31, 2006, the contents of which are hereby incorporated by referenced into the present disclosure as if fully put forth therein.

S-adenosyl methionine (SAMe) is a physiological donor of methyl groups present in all living organisms and is involved in enzyme transmethylation reactions.

This substance therefore has a very important biological role and is essentially used in clinical practice as an antidepressant.

By "SAMe" is meant both the racemic mixture and the individual diastereoisomers (RS)-(+)-S-adenosyl-L-methionine [(RS)-(+)-SAMe)] and (SS)-(+)-S-adenosyl-L-methionine [(SS)-(+)-SAMe)], as well as mixtures other than the racemic mixture.

The difficulty of using S-adenosyl methionine as a drug and/or dietetic is however known because it is extremely unstable at temperatures above 0° C. or in the presence of moisture, through both degradation of the active ingredient, understood to be the sum of the two diastereoisomers, and through the conversion of active (SS)-(+)-S-adenosyl-L-methionine to inactive (RS)-(+)-S-adenosyl-L-methionine (racemisation of the substance).

Prior methodology is thought to describes a process for the preparation of pharmaceutically acceptable salts of (SS, RS)—S-adenosyl-L-methionine with quantities of inactive diastereoisomer (RS)-(+)-S-adenosyl-L-methionine of 3% or less with respect to the active diastereoisomer (SS)-(+)-S-adenosyl-L-methionine of 97% or more. The same applies with regard to the need to use racemic mixtures with a high percentage of the active S,S diastereoisomer as this is the only one which is pharmacologically active. However, the patent confirms that although more than 97% of active S,S diastereoisomer is obtained at ambient temperature, the racemic mixture is unstable over time, with conversion of the (SS)-(+)-S-adenosyl-L-methionine into (RS)-(+)-S-adenosyl-L-methionine in a relatively short time.

Figure 1:
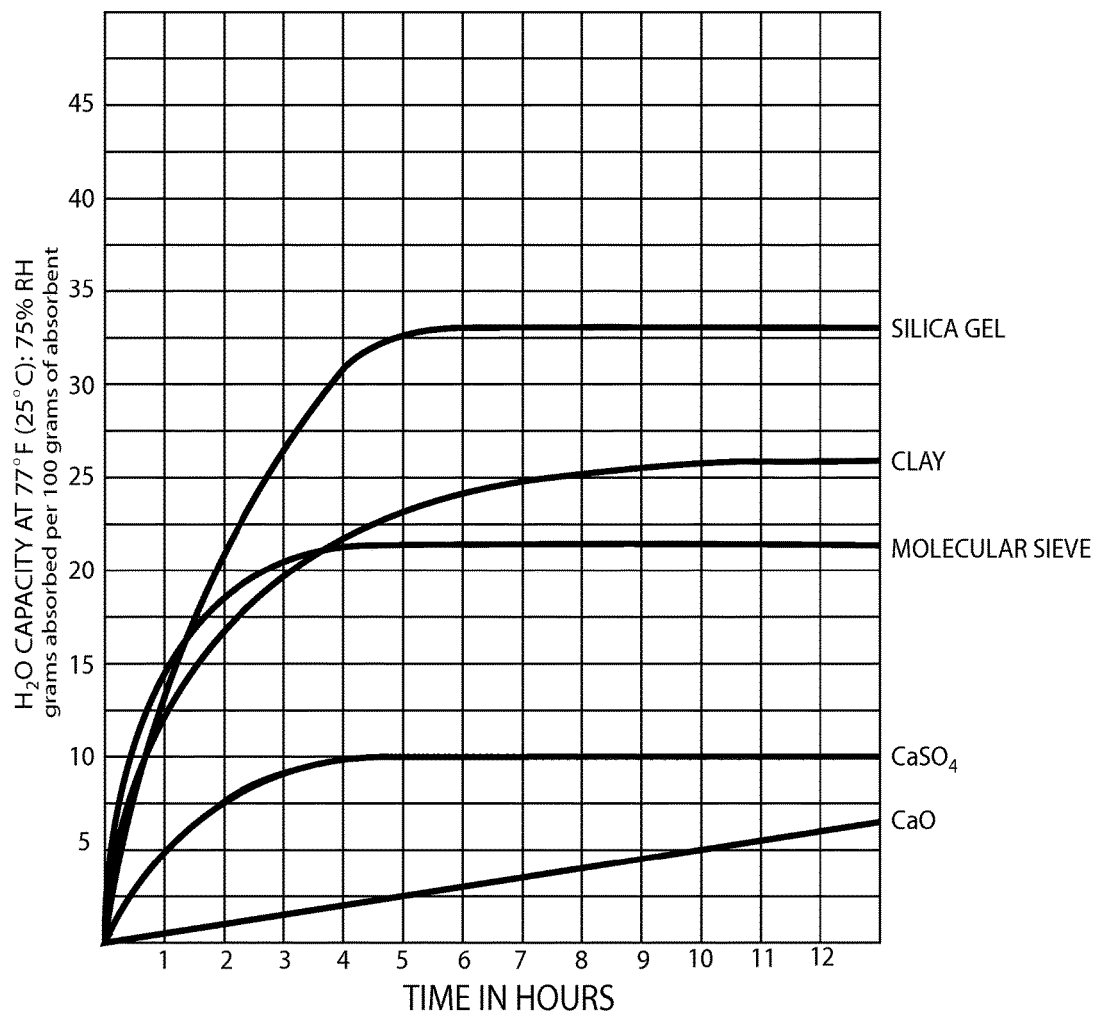
FIG. 1 represents a graph illustrating the water absorption capacity of several materials over time.

U.S. Pat. Nos. 13,627, and 98,102 describe a method for stabilising pharmaceutically acceptable salts of S-adenosyl methionine comprising S-adenosyl methionine paratoluene sulphonate, S-adenosyl methionine-1,4-butene disulphonate, S-adenosyl methionine sulphate, S-adenosyl methionine tosylate with a group of substances comprising chitosan, dextrin, carboxymethylcellulose, fumaric acid, azelaic acid and tryptophan. In particular the first of these patents indicates that it is important to have a product with the highest amount of S,S diastereoisomer which is the most stable possible over time because the R,S diastereoisomer is not only inactive but has a pharmacological effect which opposes that of the S,S. However, prior known methods are thought to describe methods for stabilising S-adenosyl methionine salts using the abovementioned substances in a percentage by weight with respect to the active ingredient which is very much higher than 50%, and adding them in reconstituted aqueous solution to S-adenosyl methionine salts, with final lyophilisation. This gives rise to high production costs and very low yields because the % of ions in the final product falls from approximately 50% to approximately 25%.

Racemisation of the S-adenosyl methionine is linked to three basic parameters:
1. The nature of S-adenosyl-L-methionine salt formation.
2. The residual moisture content in the powder after drying.
3. The temperature at which the product is stored.

The rate of racemisation of SAMe as a salt of S-adenosyl methionine paratoluene sulphonate differs from the racemisation of SAMe in the form of S-adenosyl methionine-1,4-butene disulphonate salt, or S-adenosyl methionine sulphate or as S-adenosyl methionine tosylate.

Although they have different pH for the same residual moisture content, these four salts have very different stabilities and racemisation. The reason for this has to be sought in the mechanisms of diastereoisomer degradation and conversion in the various salts.

It is known that the drier the starting material the more stable the product will be.

The same consideration applies to rate of racemisation. Theoretically, with zero moisture content, the conversion rate of the S,S diastereoisomer at a given storage temperature is at a minimum.

It is also known that the rate of degradation and therefore also racemisation is associated with the thermal energy of the material. This is reflected in the fact that the higher the storage temperature for the material, the more rapidly it degrades and racemises.

If not formulated on the basis of specific procedures and using specific measures, formulations based on S-adenosyl methionine reflect the abovementioned instability and racemisation of the active ingredient, (conversion of the active S,S diastereoisomer into the inactive R,S diastereoisomer), with obvious adverse repercussions for the preservation and storage of the material, even for short periods of time.

U.S. Pat. Nos. 3,954,726 and 4,057,672 describe relatively stable salts of S-adenosyl methionine, that is up to 25° C. and 45° C., respectively. U.S. Pat. No. 4,465,672 also describes stable salts of S-adenosyl methionine with 5 mols of a sulphonic acid with a pK of less than 2.5.

In this latter United States patent, the process of preparing the product comprises preparation of a concentrated aqueous solution of an impure salt of SAMe, purification of the solution and its elution with a dilute aqueous solution of the preselected sulphonic acid, titration of the resulting eluate, concentration and lyophilisation or spraying. Because of the high instability of SAMe and its derivatives the use of an aqueous environment makes the limitations of this process obvious, and even if residual moisture content is successfully contained it is still unsuitable because of the properties of the inactive ingredient.

Also these patents do not describe the rate of conversion of the active S,S enantiomer at various operating and storage temperatures for the product. Up to now no methods for stabilising the active (SS)-(+)-S-adenosyl-L-methionine diastereoisomer in acceptable percentages in solid oral formulations, particularly tablets, are known. The only known concept is the need to keep moisture content, impurities and the active (SS)-(+)-S-adenosyl-L-methionine diastereoisomer under strict control, protecting the tablets by either compression or film-forming.

NADH is an active ingredient normally used as an energising agent and antioxidant. Currently known compositions based on NADH, such as those for example described in U.S. Pat. Nos. 5,332,727 and 7,034,011 are based on stabilising the active ingredient through association with other antioxidants.

There has therefore hitherto been felt a need to identify a simple and economic process which will make it possible to obtain a product based on SAMe and/or NADH, with the removal of moisture and low hygroscopic properties, with as a consequence increased stability in terms of both the active ingredient and reduced racemisation in favour of stabilisation of the reduced (S,S) enantiomer and NADH.

Surprisingly it has been found that the addition of calcium oxide and/or calcium hydroxide brings about improved stability of both the SAMe, regarded as the sum of the two S,S and R,S diastereoisomers, and the (S,S) diastereoisomer and the NADH, through reducing the water content of the SAMe and the NADH and by reducing its hygroscopic properties, further favouring synergistic antidepressant action through the provision of calcium.

based on SAMe is the same in absolute terms as that present in the initial SAMe powder. As a consequence there is only a percentage reduction in moisture content in the preparations through the dilution effect, but the same percentage by weight of water with respect to the weight of SAMe used. For this reason, in a direct mixture and/or SAMe preparations, it has never hitherto been possible to achieve higher stability of the active ingredient, and therefore a reduced racemisation rate, than that of the starting material, but at the limit this stability can be achieved.

Calcium oxide is instead a natural desiccant with very high reactivity in relation to water. It reacts with it and changes to a calcium hydroxide, eliminating it permanently in preparations.

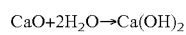

$$CaO + 2H_2O \rightarrow Ca(OH)_2$$

FIG. 1 shows the rate of absorption of $H_2O$ with different absorbent substances including calcium oxide.

It will be seen that calcium oxide absorbs slowly but constantly up to 28% of its weight.

Figure 2:
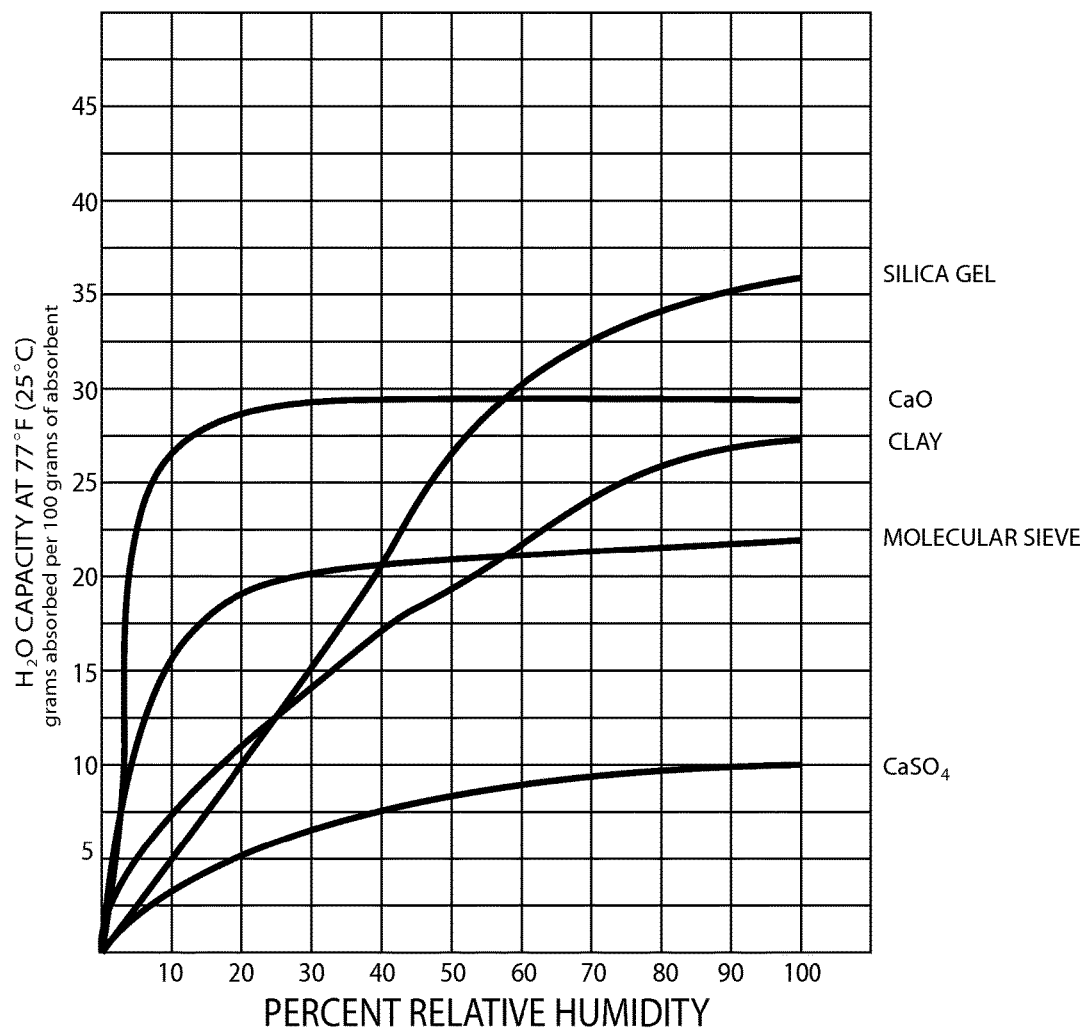
FIG. 2 illustrates the water absorbency of several materials at a varying Relative Humidity.

FIG. 2 shows the absorption capacity for water vapour of various desiccants as the environmental humidity (RH) varies.

In this case it will be seen that calcium oxide absorbs approximately 28% of water in a highly reactive way in an environment with a very low relative humidity.

Table 1 summarises the absorbent capacities of various desiccants under different relative humidity and temperature conditions.

TABLE 1

Properties of adsorbents

| Property | Molecular sieve | Silica gel | Montmorillonite clay | CaO | CaSO$_4$ |
|---|---|---|---|---|---|
| Adsorption capacity at low concentrations of H$_2$O | Excellent | Poor | Slight | Excellent | Good |
| Absorption ratio | Excellent | Good | Good | Poor | Good |
| Capacity for water @77° F. 40% RH | High | High | Medium | High | Low |
| Separation by molecular dimensions | Yes | No | No | No | No |
| Adsorption capacity at high temperatures | Excellent | Poor | Poor | Good | Good |

Calcium oxide and/or hydroxide directly mixed with atomised SAMe and/or NADH powder, or with solid formulations based on SAMe and/or NADH, are successful in removing water through a chemical reaction with the powder or the preparation itself.

In fact no other excipients which succeed in removing moisture in direct mixture with the powder and/or preparations of SAMe and/or NADH over time at relatively lower temperatures (15-20° C.), reaching values of close to zero, are known.

The main reason is due to the highly hygroscopic nature of the SAMe which is even greater than that of substances which are well known as excellent desiccants such as silica gel, calcium chloride and others. This means that by mixing SAMe with excipients having a moisture content of close to zero, the residual water in mixtures and/or preparations Specifically the shape of the two FIGS. 1 and 2 and the summary values in Table 1 demonstrate that calcium oxide is the only substance which is consistently capable of removing the very small quantities of residual moisture content of SAMe or the relatively high moisture content of NADH, or its salts (approximately 1-1.5% K.F./approximately 5-7% K.F.) by chemical conversion purely by physical contact, reducing it to values close to zero.

This therefore reduces the second instability factor in SAMe, or its salts, because of the high rate of racemisation of its active S,S diastereoisomer. Table 2 provides moisture content values for five lots of starting material of SAMe (S-adenosyl methionine paratoluene sulphonate) with its corresponding analysis prior to mixing with calcium oxide and storage at 20° C. for 21 days, and the relative accelerated stability at 53° C. for 5 days.

TABLE 2 stress test 5 days at 53° C.

| Lot | Moisture content % K.F. t = 0 | Moisture content % K.F. t = 21 days at 20° C. | % S,S t = 0 | SAMe titre % t = 0 | Total impurities % t = 0 | Moisture content % K.F. | % S,S | SAMe titre % | Total impurities % |
|---|---|---|---|---|---|---|---|---|---|
| 001 | 1.15 | 1.13 | 80.87 | 52.96 | 0.66 | 1.09 | 56.21 | 51.19 | 5.17 |
| 002 | 1.08 | 1.05 | 80.02 | 51.98 | 0.73 | 1.05 | 56.31 | 50.84 | 5.54 |
| 003 | 1.06 | 1.03 | 80.21 | 52.76 | 1.03 | 1.03 | 56.12 | 50.11 | 4.55 |
| 004 | 1.09 | 1.09 | 79.82 | 52.23 | 0.94 | 0.99 | 55.79 | 49.58 | 4.34 |
| 005 | 1.04 | 1.12 | 81.54 | 52.29 | 1.04 | 1.00 | 55.28 | 49.99 | 5.02 |

Table 3 shows moisture content values for five lots of starting material of SAMe (S-adenosyl methionine paratoluene sulphonate) with its corresponding analysis after mixing with calcium oxide and storage at 20° C. for 21 days, and the relative accelerated stability at 53° C. for 5 days.

TABLE 3

Stress test 5 days at 53° C.

| Lot | Moisture content % K.F. t = 0 | Moisture content % K.F. t = 21 days at 20° C. | % S,S t = 0 | SAMe titre % t = 0 | Total impurities % t = 0 | Moisture content % K.F. | % S,S | SAMe titre % | Total impurities % |
|---|---|---|---|---|---|---|---|---|---|
| 001 | 0.98 | 0.63 | 80.67 | 50.22 | 0.66 | 0.43 | 66.47 | 50.09 | 3.17 |
| 002 | 1.16 | 0.55 | 80.32 | 50.02 | 0.73 | 0.41 | 65.43 | 50.00 | 2.78 |
| 003 | 1.00 | 0.70 | 80.11 | 50.16 | 1.03 | 0.39 | 66.56 | 49.81 | 2.65 |
| 004 | 1.04 | 0.59 | 79.99 | 50.23 | 0.94 | 0.35 | 65.79 | 49.98 | 2.89 |
| 005 | 0.95 | 0.61 | 81.23 | 50.19 | 1.04 | 0.38 | 67.25 | 49.87 | 3.02 |

Table 4 shows moisture content values for five lots of starting material of SAMe (S-adenosyl methionine-1,4-butene disulphonate) with corresponding analysis prior to mixing with calcium oxide and storage at 20° C. for 21 days, and the relative accelerated stability at 53° C. for 5 days.

TABLE 4

Stress test 5 days at 53° C.

| Lot | Moisture content % K.F. t = 0 | Moisture content % K.F. t = 21 days at 20° C. | % S,S t = 0 | SAMe titre % t = 0 | Total impurities % t = 0 | Moisture content % K.F. | % S,S | SAMe titre % | Total impurities % |
|---|---|---|---|---|---|---|---|---|---|
| 001 | 2.03 | 2.03 | 84.58 | 51.34 | 0.44 | 2.09 | 59.43 | 50.94 | 4.06 |
| 002 | 2.01 | 2.31 | 85.34 | 51.54 | 0.56 | 2.21 | 60.02 | 50.93 | 4.23 |
| 003 | 1.98 | 1.99 | 83.89 | 52.34 | 0.45 | 2.00 | 60.32 | 51.03 | 4.05 |
| 004 | 1.89 | 1.99 | 84.82 | 52.02 | 0.67 | 1.96 | 59.49 | 51.72 | 4.63 |
| 005 | 1.94 | 2.02 | 85.34 | 51.78 | 0.64 | 1.93 | 58.98 | 50.79 | 4.47 |

Table 5 shows moisture content values for five lots of starting material of SAMe (S-adenosyl methionine-1,4-butene disulphonate) with corresponding analysis after mixing with calcium oxide and storage for 23° C. for 21 days, and the relative accelerated stability at 53° C. for 5 days.

TABLE 5

Stress test 5 days at 53° C.

| Lot | Moisture content % K.F. t = 0 | Moisture content % K.F. t = 21 days at 20° C. | % S,S t = 0 | SAMe titre % t = 0 | Total impurities % t = 0 | Moisture content % K.F. | % S,S | SAMe titre % | Total impurities % |
|---|---|---|---|---|---|---|---|---|---|
| 001 | 1.94 | 1.33 | 84.21 | 50.01 | 0.49 | 0.78 | 70.34 | 50.00 | 2.03 |
| 002 | 1.89 | 1.45 | 85.02 | 49.78 | 0.50 | 0.87 | 70.02 | 50.01 | 1.98 |
| 003 | 1.87 | 1.27 | 83.49 | 50.12 | 0.49 | 0.93 | 71.32 | 49.89 | 2.00 |

TABLE 5-continued

Stress test 5 days at 53° C.

| Lot | Moisture content % K.F. t = 0 | Moisture content % K.F. t = 21 days at 20° C. | % S,S t = 0 | SAMe titre % t = 0 | Total impurities % t = 0 | Moisture content % K.F. | % S,S | SAMe titre % | Total impurities % |
|---|---|---|---|---|---|---|---|---|---|
| 004 | 1.80 | 1.38 | 84.54 | 50.34 | 0.57 | 0.81 | 71.89 | 50.04 | 2.13 |
| 005 | 1.84 | 1.40 | 85.25 | 50.08 | 0.53 | 0.88 | 70.94 | 50.00 | 1.35 |

Table 6 shows moisture content values for five lots of starting material of NADH with corresponding analysis prior to mixing with calcium oxide and storage at 20° C. for 21 days, and the relative accelerated stability at 53° C. for 5 days.

TABLE 6

Stress test 5 days at 53° C.

| Lot | Moisture content % K.F. t = 0 | Moisture content % K.F. t = 21 days at 20° C. | NADH (sodium salt) titre % t = 0 | Total impurities % t = 0 | Moisture content % K.F. | NADH (sodium salt) titre % t = 0 | Total impurities % |
|---|---|---|---|---|---|---|---|
| 001 | 6.45 | 6.34 | 92.43 | 1.66 | 6.09 | 82.19 | 7.17 |
| 002 | 6.38 | 6.32 | 91.98 | 1.73 | 6.05 | 83.84 | 7.54 |
| 003 | 6.66 | 6.34 | 92.73 | 1.33 | 6.23 | 83.11 | 8.55 |
| 004 | 7.09 | 6.87 | 92.23 | 1.44 | 6.54 | 84.58 | 7.34 |
| 005 | 5.94 | 5.76 | 92.45 | 1.64 | 5.00 | 83.99 | 7.02 |

Table 7 shows moisture content values for five lots of starting material of NADH with corresponding analysis after mixing with calcium oxide and storage at 20° C. for 21 days, and the relative accelerated stability at 53° C. for 5 days.

TABLE 7

Stress test 5 days at 53° C.

| Lot | Moisture content % K.F. t = 0 | Moisture content % K.F. t = 21 days at 20° C. | NADH (sodium salt) titre % t = 0 | Total impurities % t = 0 | Moisture content % K.F. | NADH (sodium salt) titre % t = 0 | Total impurities % |
|---|---|---|---|---|---|---|---|
| 001 | 6.21 | 3.20 | 84.53 (*) | 1.50 | 3.49 | 81.19 | 2.45 |
| 002 | 6.33 | 4.32 | 85.32 (*) | 1.48 | 3.45 | 82.34 | 3.54 |
| 003 | 6.44 | 4.01 | 83.93 (*) | 1.44 | 3.23 | 80.56 | 2.67 |
| 004 | 7.23 | 4.39 | 84.23 (*) | 1.54 | 3.54 | 82.56 | 3.14 |
| 005 | 6.87 | 3.98 | 83.95 (*) | 1.43 | 3.10 | 82.49 | 3.02 |

(*) Lower titre because mixed with 10% of calcium oxide.

From the data shown in Tables 2, 3, 4, 5, 6, 7 it will be seen that the mixture of calcium oxide in combination with SAMe (S-adenosyl methionine paratoluene sulphonate and S-adenosyl methionine-1,4-butene disulphonate) or with NADH causes the stability of the material at 53° C. for 5 days to increase with permanent removal of approximately 40% of the moisture content when the mixture is stored for 21 days at 20° C., and approximately 60% after the stress test at 53° C. for 5 days.

Thus, one object of this invention relates to compositions comprising SAMe and/or NADH, or their salts, in association with calcium oxide and/or calcium hydroxide, and optionally pharmaceutically acceptable excipients.

According to this invention, by "SAMe" is meant both the racemic mixture and the individual (RS)-(+)-S-adenosyl-L-methionine [(RS)-(+)-SAMe] and (SS)-(+)-S-adenosyl-L-methionine [(SS)-(+)-SAMe] diastereoisomers, including the mixtures other than the racemic mixture. In particular, the compositions according to this invention contain SAMe, or its salts, in a quantity of between 30 and 90% by weight, preferably between 50 and 85% by weight, with respect to the weight of the composition, in association with calcium oxide and/or calcium hydroxide in a quantity of between 1 and 40% by weight, preferably between 2 and 20% by weight, with respect to the weight of the composition.

In particular, the compositions according to this invention contain NADH, or its salts, in a quantity between 1 and 90% by weight, preferably between 5 and 50% by weight, with respect to the weight of the composition, in association with calcium oxide and/or calcium hydroxide in a quantity of between 1 and 40% by weight, preferably between 2 and 20% by weight, with respect to the weight of the composition.

Preferably the said SAMe, or its salts, is S-adenosyl methionine paratoluene sulphonate, S-adenosyl methionine-1,4-butene disulphonate, S-adenosyl methionine sulphate, S-adenosyl methionine tosylate.

Preferably, the NADH is present in the form of its pharmaceutically acceptable salts.

Preferably the said calcium oxide and/or calcium hydroxide is calcium oxide alone, calcium hydroxide alone, or a mixture thereof.

The pharmaceutically acceptable excipients used according to this invention are preferably selected from calcium sulphate hemihydrate, magnesium oxide, malic acid, glutamic acid, glucono-delta-lactone, xylitol and/or their mixtures.

Compositions according to this invention may optionally comprise at least one further active ingredient, preferably selected from melatonin, 1-theanine and/or 1-tryptophan and/or 5-hydroxytryptophan and/or their mixtures.

The compositions according to this invention may be in the form of a direct mixture, tablets, capsules, granules and/or powder. In this invention by direct mixture is meant a mixture of atomised powder of SAMe and/or NADH, or their salts, in association with calcium oxide and/or calcium hydroxide alone, without the addition of other excipients.

Preferably, the compositions according to this invention are in the form of tablets, more preferably in the form of ordinary, coated, film-coated and/or gastroresistant tablets.

In this invention, by ordinary tablet is meant a tablet obtained by direct compression or compression after granulation without coating; by coated tablet is meant a tablet coated with non-gastroresistant substances; by film-coated tablet is meant a coated tablet which is further covered with water-based varnishes, which varnishes may have a gastroresistant action.

Thus, the compositions according to this invention may be film-coated with water-based varnishes preferably selected from gum Lac (Shellac™) and/or its salts, methacrylic acid, cellulose acetophthalates, titanium dioxide, talc, triethyl citrate, PVP K30, curcumin, lutein, hydroxypropylcellulose, hydroxypropylmethylcellulose and/or mixtures thereof.

By gastroresistant tablets according to this invention are meant tablets capable of passing unchanged through the gastric barrier.

The said film coating with varnishes, when provided through Shellac™ salts, cellulose acetophthalates and/or other coatings which are insoluble in an acid environment, may render the compositions according to the invention resistant to passage through the stomach. The varnishes according to this invention may be present in a quantity varying from 1.0 to 1.98% by weight with respect to the composition.

The compositions according to this invention have approximately 60% less moisture content (KF) than the compositions based on SAMe known hitherto and are approximately 12 times less hygroscopic than shown in Table 6 above.

TABLE 8

| Known tablets based on SAMe SAMe 400 mg tablets KF % T = 0 | Known tablets based on SAMe SAMe 400 mg tablets KF % T = 24 h* | SAMe/CaO tablets (Example 1) KF % T = 0 | SAMe/CaO tablets (Example 1) KF % T = 24 h* |
|---|---|---|---|
| Lot 01 1.24 | 3.76 | 0.45 | 0.76 |
| Lot 02 1.21 | 3.87 | 0.51 | 0.68 |
| Lot 03 1.10 | 3.98 | 0.52 | 0.70 |
| Lot 04 1.33 | 3.75 | 0.43 | 0.64 |
| Lot 05 1.39 | 3.76 | 0.57 | 0.74 | at 40° C. −75Rh KF (moisture content according to the Karl Fischer method)
T = time The compositions according to this invention are preferably intended for the treatment of depressive states.

A further object of this invention is a process for the preparation of solid compositions for oral use comprising SAMe and/or NADH, or their salts, in association with calcium oxide and/or calcium hydroxide which comprises the following stages:
  a) mixing of the SAMe, or its salts, with calcium oxide and pharmaceutically acceptable excipients,
  b) precompression and subsequent granulation of the mixture obtained in stage a),
  c) mixing of the granulate obtained in stage b) with pharmaceutically acceptable excipients such as calcium sulphate hemihydrate, xylitol, malic acid, glutamic acid, magnesium oxide, hydrogenated fatty acids, precipitated silica, magnesium stearate, saccharose, glycerol behenate,
  d) compression of the mixture obtained in stage c), with the optional addition of sweeteners and/or flavourings,
  e) optional coating of the tablet obtained in stage d) with hydrogenated fatty acids,
  f) optional aqueous phase film-forming on the tablet obtained in stage e).

The process according to this invention is carried out in an environment in which the relative humidity lies below 20% and the temperature is held between 18 and 25° C., preferably around 20° C.

Granulation according to this invention is preferably carried out using a rotating blade granulator fitted with a stainless mesh having holes of between 1.2 mm and 3.2 mm in diameter.

SAMe, or its salts, is used in a quantity varying from 30 to 90% by weight, preferably from 50 to 85% by weight, with respect to the weight of the composition.

NADH, or its salts, is used in a quantity varying from 1 to 90% by weight, preferably from 5 to 50% by weight, with respect to the weight of the composition.

In particular, the pharmaceutically acceptable excipients used in the process according to the invention are preferably selected from calcium sulphate hemihydrate, magnesium oxide, calcium carbonate, malic acid, glutamic acid, xylitol, saccharose, anhydrous microcrystalline cellulose, hydrogenated fatty acids, magnesium stearate, glycerol behenate, precipitated silica.

More particularly, in step a) the active ingredient is preferably mixed with calcium oxide from approximately 1.0 to approximately 10% by weight and/or magnesium stearate from approximately 0.5 to approximately 5% by weight and/or precipitated silica from approximately 0.5 to approximately 2.0% by weight calculated with respect to the active ingredient.

In stage c), the granulate obtained in b) is preferably mixed with magnesium hydroxide from approximately 1.0 to 10.0% by weight and/or microcrystalline cellulose from approximately 1.0 to approximately 20.0% by weight and/or hydrogenated fatty acids from approximately 1.0 to approximately 10% by weight and/or malic acid from approximately 1 to approximately 10% by weight and/or glutamic acid from approximately 1 to approximately 10% by weight and/or glucono-delta-lactone from approximately 1 to approximately 10% by weight, magnesium stearate from approximately 0.5 to approximately 5% by weight and/or glycerol behenate from approximately 1.0 to approximately 5.0% calculated with respect to the active ingredient.

Optionally, in said stage c) of the process according to the invention at least one further active ingredient preferably selected from melatonin, 1-theanine and/or 1-tryptophan and/or 5-hydroxytryptophan and/or their mixtures may be added to the mixture for the treatment of depressive states.

At stage e) coating with hydrogenated fatty acids, preferably molten hydrogenated vegetable fatty acids, may be performed using conventional processes known in the art, with if appropriate the addition of surfactants which are miscible in the oily liquid.

According to this invention the coating mentioned in stage e) may be performed using hydrogenated fatty acids, preferably molten hydrogenated vegetable fatty acids, in a quantity of between approximately 0.4 and approximately 1.5% by weight with respect to the weight of the composition.

The said stage h) in the process according to this invention, makes it possible to reduce the hygroscopic nature of the tablet obtained in stage g) by approximately twelve times, bringing about appreciable advantages in any subsequent stage of aqueous phase film-forming.

Aqueous phase film-forming (stage i) may be carried out using a substance or varnish preferably selected from gum Lac (Shellac™) and/or its salts, methacrylic acid, cellulose acetophthalates, titanium dioxide, talc, triethyl citrate, PVP K30, curcumin, lutein, hydroxypropylcellulose, hydroxypropylmethylcellulose and/or mixtures thereof.

In particular the said film-forming may be carried out using substances preferably selected from gum Lac (Shellac™) and/or its salts.

A further object of this invention is the use of SAMe or its salts in association with calcium and magnesium for the preparation of pharmaceutical, dietetic and/or nutritional/pharmaceutical compositions for the treatment of depressive states.

Yet a further object of this invention is a method for stabilising SAMe and/or NADH, preferably the (S,S) enantiomer, or its salts, which comprises the use of calcium oxide and/or calcium hydroxide in the percentages indicated above.

EXAMPLES

Example 1

Tablets of 400 mg SAMe Ion/Tablet
Composition Based on SAMe Sulphate p-Toluene Sulphonate

| | |
|---|---|
| A. SAMe sulphate p-toluene sulphonate | 800.00 mg |
| B Calcium oxide | 70.00 mg |
| C. Magnesium hydroxide | 80.00 mg |
| D. Saccharose | 100.00 mg |
| E. Calcium carbonate | 80.00 mg |
| F. Magnesium stearate | 20.00 mg |
| G. Malic acid | 40.00 mg |
| E. Hydrogenated fatty acid | 50.00 mg |
| Total weight of core | 1240.00 mg |
| F. Hydrogenated vegetable fatty acids | 4.00 mg |
| G. Shellac ® | 30.00 mg |
| H. PVP K 30 | 6.0 mg |
| I. Titanium dioxide | 5.00 mg |
| L. Talc | 10.00 mg |
| M. Triethyl citrate | 5.00 mg |
| N. Curcumin | 0.050 mg |
| Total weight of tablet | 1300.50 mg |

1.1. Mixing

The working environment was conditioned to a temperature of 20° C. and a relative humidity value of approximately 20% RH. A, B, C, D, E and G and 50% of F were then transferred to the mixer in the quantities indicated above, leaving them with stirring for approximately 30 minutes. At the end of this operation the resulting mixture was transferred to dry containers, always controlling moisture content and temperature.

1.2. Precompression

Precompression of the mixture was effected using a rotary machine equipped with round punches of 25.0 mm. The hardness of the tablets produced had to be regulated to subsequently produce a granulate having good flow characteristics.

1.3 Granulation

The tablets produced during the first processing stage were granulated on a 1000-1500 µm mesh, again in a humidity-controlled environment.

1.4 Mixing

The granulate obtained in stage 1.3 was transferred into the mixer, adding magnesium stearate and leaving it with stirring for approximately 30 minutes. At the end of this operation the resulting mixture was transferred into dry containers.

1.5 Compression

Final compression of the granulate was carried out using a rotary machine equipped with oblong punches of 21.0×9 8 mm adjusting the weight to 1240 mg/tablet and the compression force to at least 25 KP. The tablets produced had a hardness of between 25 and 35 Kp.

Friability: ≤1.0%; disaggregation time: ≤15 minutes (measured using the method described in U.S.P. 24$^{th}$ ed.)

Moisture content according to K.F.≤1.50%

Stability tests on uncoated tablets were performed at only 40° C. and 75% RH for six months and for a single lot because this is not a finished product. The samples were stored in alu/alu blisters.

TABLE 9

Lot 001 - cores of 400 mg ion/tablet (qualitative/quantitative composition in Example 1)

| Lot (T/t)[1] | Moisture content % (K. Fischer) | S,S % | AD[2] (%) | MTAD[3] (%) | SAMe[4] |
|---|---|---|---|---|---|
| 001 (20/0) | 0.66 | 79.9 | 0.21 | 0.43 | 409.98 |
| 001A (40/1) | 0.56 | 75.7 | 0.33 | 0.67 | 409.58 |
| 001B (40/3) | 0.44 | 72.5 | 0.54 | 0.78 | 407.02 |
| 001C (40/6) | 0.35 | 70.3 | 0.76 | 0.98 | 404.78 |

[1]Temperature (° C.)/time (months);
[2]adenosine;
[3]methylthioadenosine;
[4]SAMe sulphate p-toluene sulphonate (mg/tablet);

The data in Table 9 show that the tablets have optimum stability.

1.6: Tablet Coating

The tablets resulting from the preceding processing stages were coated in a bowl with a mixture of hydrogenated fatty acids (4.0 mg/tablet).

Hydrogenated fatty acid melting at 70° C. was placed in a glass container of 2.0 litres and the temperature of the mixture was raised to approximately 75° C. obtaining a homogeneous fused mass.

After the bowl had been preheated to approximately 65° C., approximately 250 kg of tablets were added and allowed to heat up to 60° C. The cores were then protected by causing the previously prepared fused mass to adhere to the moving tablets. The cores so treated were again left at 60°

C. for approximately 3 minutes, until the waxy layer had been completely cleaned from the basket of the bowl.

1.7: Film-Forming on the Tablets

Shellac™ and PVP were dissolved in a container of suitable size until a solution of 20% w/v was obtained, and triethyl citrate was added slowly with constant stirring.

In another steel container again fitted with a stirrer, talc, titanium dioxide and curcumin were dispersed in 4.0 l of deionised water. The resulting suspension was poured into the Shellac™ solution, washing the container with approximately 1.0 l of deionised water, subsequently diluting with a further 4.0 l of deionised water.

During the first coating stage the temperature of the cores was held at 54° C. for approximately 40 minutes, and this was then reduced in regular steps down to a value of 45° C. in the final stage.

After coating of the protected cores was complete, they were allowed to dry for a further 10 minutes, again at 45° C. Finally reduction in the temperature to 42-43° C. was awaited so that emptying of the bowl could begin, taking care to store the tablets in suitable envelopes which were impermeable to moisture. No increase in percentage water content was observed in the tablets produced in this way. All the checks specified by the quality specifications were also carried out on these.

Example 2

Tablets of 400 mg SAMe Ion/Tablet
Compositions Based on SAMe Sulphate p-Toluene Sulphonate

| | |
|---|---|
| A. SAMe sulphate p-toluene sulphonate | 800.00 mg |
| B. L-melatonin | 2.00 mg |
| C Calcium oxide | 70.00 mg |
| D. Magnesium hydroxide | 100.00 mg |
| E. Calcium sulphate hemihydrate | 100.00 mg |
| F. Calcium carbonate | 160.00 mg |
| G. Magnesium stearate | 20.00 mg |
| H. Malic acid | 40.00 mg |
| I. Hydrogenated fatty acid | 40.00 mg |
| Total weight of core | 1332.00 mg |
| L. Hydrogenated vegetable fatty acids | 4.00 mg |
| M. Shellac ® | 30.00 mg |
| N. PVP K 30 | 6.0 mg |
| O. Titanium dioxide | 5.00 mg |
| P. Talc | 10.00 mg |
| Q. Triethyl citrate | 5.00 mg |
| R. Curcumin | 0.050 mg |
| Total weight of tablet | 1302.50 mg |

The quantities relate to the preparation of a standard industrial lot of 250.00 kg of tablets.

The tablets were prepared in the manner described in Example 1 using the components and quantities indicated above.

TABLE 10

Lot 002 - cores of 400 mg/ion/tablet (qualitative/quantitative composition in Example 2)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 002 (20/0) | 0.71 | 81.2 | 0.29 | 0.39 | 413.11 | 2.04 |
| 002A (40/1) | 0.50 | 76.8 | 0.35 | 0.58 | 410.21 | 2.03 |
| 002B (40/3) | 0.52 | 73.0 | 0.49 | 0.65 | 411.54 | 2.03 |
| 002C (40/6) | 0.42 | 71.0 | 0.79 | 0.83 | 409.40 | 2.01 |

[1]Temperature (° C.)/time (months);
[2]adenosine;
[3]methylthioadenosine;
[4]SAMe sulphate p-toluene sulphonate (mg/tablet);

The data in Table 10 indicate that the tablets have optimum stability.

Example 3

Tablets of 400 mg SAMe Ion/Tablet
Composition Based on SAMe Sulphate p-Toluene Sulphonate

| | |
|---|---|
| A. SAMe sulphate p-toluene sulphonate | 800.00 mg |
| B. L-theanine | 200.00 mg |
| C Calcium oxide | 70.00 mg |
| D. Magnesium hydroxide | 100.00 mg |
| E. Xylitol | 50.00 mg |
| F. Calcium carbonate | 100.00 mg |
| G. Microcrystalline cellulose | 60.00 mg |
| H. Magnesium stearate | 20.00 mg |
| I. Malic acid | 40.00 mg |
| L. Hydrogenated fatty acid | 40.00 mg |
| Total weight of core | 1480.00 mg |
| M. Hydrogenated vegetable fatty acids | 4.00 mg |
| N. Shellac ® | 30.00 mg |
| O. PVP K 30 | 6.0 mg |
| P. Titanium dioxide | 5.00 mg |
| Q. Talc | 10.00 mg |
| R. Triethyl citrate | 5.00 mg |
| S. Hydroxypropylmethylcellulose | 10.00 mg |
| T. Curcumin | 0.050 mg |
| Total weight of tablet | 1550.05 mg |

The quantities relate to the preparation of a standard industrial lot of 250.00 kg of tablets.

The tablets were prepared in the manner described in Example 1 using the components and quantities indicated above.

TABLE 11

Lot 003 - cores of 400 mg ion/tablet (qualitative/quantitative composition in Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 003 (20/0) | 0.59 | 80.4 | 0.23 | 0.34 | 411.32 | 204.54 |
| 003A (40/1) | 0.53 | 76.6 | 0.32 | 0.61 | 410.54 | 203.54 |

TABLE 11-continued

Lot 003 - cores of 400 mg ion/tablet (qualitative/quantitative composition in Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 003B (40/3) | 0.45 | 73.4 | 0.45 | 0.72 | 410.02 | 203.01 |
| 003C (40/6) | 0.37 | 71.3 | 0.69 | 0.88 | 407.56 | 201.92 |

[1]Temperature (° C.)/time (months);
[2]adenosine;
[3]methylthioadenosine;
[4]SAMe sulphate p-toluene sulphonate (mg/tablet);

The data in Table 11 show that the tablets have optimum stability.

Example 4

Tablets of 400 mg SAMe Ion/Tablet
Composition Based on SAMe Sulphate p-Toluene Sulphonate

| A. SAMe sulphate p-toluene sulphonate | 800.00 mg |
|---|---|
| B Calcium oxide | 70.00 mg |
| C. Magnesium hydroxide | 100.00 mg |
| D. Calcium carbonate | 150.00 mg |
| E. Magnesium stearate | 20.00 mg |
| F. Malic acid | 40.00 mg |
| G. Hydrogenated fatty acid | 40.00 mg |
| Total weight of core | 1220.00 mg |
| H. Hydrogenated vegetable fatty acids | 8.00 mg |
| I. Hydroxypropylmethylcellulose | 30.00 mg |
| L. PVP K 30 | 6.0 mg |
| M Titanium dioxide | 5.00 mg |
| N. Talc | 10.00 mg |
| O. Triethyl citrate | 5.00 mg |
| P. Curcumin | 0.050 mg |
| Total weight of tablet | 1284.05 mg |

The quantities relate to the preparation of a standard industrial lot of 250.00 kg of tablets.

The tablets were prepared in the manner described in Example 1 using the components and quantities indicated above.

Example 5

Tablets of 400 mg SAMe Ion/Tablet
Composition Based on SAMe Sulphate p-Toluene Sulphonate

| A. SAMe sulphate p-toluene sulphonate | 800.00 mg |
|---|---|
| B. Folic acid | 3.00 mg |
| C Calcium oxide | 70.00 mg |
| D. Magnesium hydroxide | 100.00 mg |
| E. Calcium carbonate | 100.00 mg |
| F. Calcium sulphate | 100.00 mg |
| G. Magnesium stearate | 20.00 mg |
| H. Malic acid | 40.00 mg |
| I. Hydrogenated fatty acid | 40.00 mg |
| Total weight of core | 1273.00 mg |
| L. Hydrogenated vegetable fatty acids | 8.00 mg |
| M. Hydroxypropylmethylcellulose | 30.00 mg |
| N. PVP K 30 | 6.0 mg |
| O Titanium dioxide | 5.00 mg |
| P. Talc | 10.00 mg |
| Q. Triethyl citrate | 5.00 mg |
| R. Curcumin | 0.050 mg |
| Total weight of tablet | 1284.05 mg |

The quantities relate to the preparation of a standard industrial lot of 250.00 kg of tablets.

The tablets were prepared in the manner described in Example 1 using the components and quantities indicated above.

TABLE 12

Lot 004 - cores of 400 mg ion/tablet (qualitative/quantitative composition in Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 004 (20/0) | 0.59 | 80.11 | 0.33 | 0.23 | 410.89 | 3.23 |
| 004A (40/1) | 0.53 | 75.4 | 0.45 | 0.55 | 410.43 | 3.24 |
| 004B (40/3) | 0.45 | 72.8 | 0.55 | 0.67 | 409.76 | 3.21 |
| 004C (40/6) | 0.37 | 69.6 | 0.79 | 0.99 | 408.67 | 3.19 |

[1]Temperature (° C.)/time (months);
[2]adenosine;
[3]methylthioadenosine;
[4]SAMe sulphate p-toluene sulphonate (mg/tablet);

The data in Table 12 indicate that the tablets have optimum stability.

Example 6

Tablets of 400 mg SAMe Ion/Tablet
Composition Based on SAMe Sulphate p-Toluene Sulphonate

| A. SAMe sulphate p-toluene sulphonate | 800.00 mg |
|---|---|
| B. Folic acid | 3.00 mg |
| C. Melatonin | 2.00 mg |
| C Calcium oxide | 70.00 mg |
| D. Magnesium hydroxide | 100.00 mg |
| E. Calcium carbonate | 100.00 mg |
| F. Calcium sulphate | 100.00 mg |
| G. Magnesium stearate | 20.00 mg |
| H. Malic acid | 40.00 mg |
| I. Hydrogenated fatty acid | 40.00 mg |
| Total weight of core | 1275.00 mg |

The quantities relate to the preparation of a standard industrial lot of 250.00 kg of tablets.

The tablets were prepared in the manner described in Example 1 using the components and quantities indicated above.

TABLE 13

Lot 005 - cores of 400 mg ion/tablet (qualitative/quantitative composition in Example 6).

| Lot (T/t)[1] | Moisture content % (K. Fischer) | S,S % | AD[2] (%) | MTAD[3] (%) | SAMe[4] | Folic acid mg | L-melatonin mg |
|---|---|---|---|---|---|---|---|
| 005 (20/0) | 0.53 | 81.3 | 0.29 | 0.40 | 415.12 | 3.12 | 2.21 |
| 005A (40/1) | 0.50 | 76.2 | 0.38 | 0.59 | 414.21 | 3.03 | 2.12 |

TABLE 13-continued

Lot 005 - cores of 400 mg ion/tablet (qualitative/quantitative composition in Example 6).

| Lot (T/t)[1] | Moisture content % (K. Fischer) | S,S % | AD[2] (%) | MTAD[3] (%) | SAMe[4] | Folic acid mg | L-melatonin mg |
|---|---|---|---|---|---|---|---|
| 005B (40/3) | 0.41 | 73.2 | 0.51 | 0.73 | 413.34 | 3.02 | 2.04 |
| 005C (40/6) | 0.29 | 69.2 | 0.83 | 1.09 | 412.21 | 3.00 | 2.08 |

[1]Temperature (° C.)/time (months);
[2]adenosine;
[3]methylthioadenosine;
[4]SAMe sulphate p-toluene sulphonate (mg/tablet);

The data in Table 13 reveal that the tablets have optimum stability.

Example 7

Tablets of 5.5 mg of NADH/Tablet as Sodium Salt Compositions Based on NADH without Calcium Oxide

| DESCRIPTION OF COMPONENTS | | QUANTITY PER UNIT |
|---|---|---|
| Active ingredient | | |
| A) NADH | mg | 5.50 |
| Excipients (core) | | |
| B) Microcrystalline cellulose | mg | 7.00 |
| C) Mannitol | mg | 26.0 |
| D) Glycerol behenate | mg | 2.00 |
| E) "Light" magnesium oxide* | mg | 8.0 |
| F) Magnesium stearate | mg | 0.50 |
| G) Calcium carbonate | mg | 1.00 |
| Total weight of core | mg | 50.00 |
| Excipients (coating) | | |
| H) Schellac | mg | 2.00 |
| I) Povidone (PVP) | mg | 0.20 |
| L) Titanium dioxide | mg | 0.10 |
| M) Anhydrous colloidal silica | mg | 0.20 |
| N) Talc | mg | 0.20 |
| O) Triethyl citrate | mg | 0.15 |
| Overall weight of the coated tablets | mg | 52.85 |

*= Magnesium oxide light is a better lubricant than the heavy form

Example 8
Tablets of 5.5 mg of NADH/Tablet as Sodium Salt Composition Based on NADH with Calcium Oxide

| DESCRIPTION OF COMPONENTS | | QUANTITY PER UNIT |
|---|---|---|
| Active ingredient | | |
| A) NADH | mg | 5.50 |
| Excipients (core) | | |
| B) Microcrystalline cellulose | mg | 7.00 |
| C) Mannitol | mg | 20.0 |
| D) Glycerol behenate | mg | 2.00 |
| E) Calcium oxide | mg | 6.00 |
| F) "Light" magnesium oxide* | mg | 8.00 |
| G) Magnesium stearate | mg | 0.50 |
| H) Calcium carbonate | mg | 1.00 |
| Total weight of core | mg | 50.00 |
| Excipients (coating) | | |
| I) Schellac | mg | 2.00 |
| L Povidone (PVP) | mg | 0.20 |
| M) Titanium dioxide | mg | 0.10 |
| N) Anhydrous colloidal silica | mg | 0.20 |
| O) Talc | mg | 0.20 |
| P) Triethyl citrate | mg | 0.15 |
| Overall weight of the coated tablets | mg | 52.85 |

*= Magnesium oxide light is a better lubricant than the heavy form

The quantities relate to the preparation of a standard industrial lot of 20.00 kg of tablets Experimental Part Stability Tests on the Finished Product Stability at 40° C. 75% RH (STRESS TEST) and at ambient temperature over a long period (SHELF LIFE) for the compositions in Examples 1, 2, 3, 4, 5, 6, 7, 8 obtained according to the process according to the invention were evaluated for changes in appearance (essentially change in colour), titre of SAMe sulphate p-toluene sulphonate and NADH and other active ingredients (mg/tablet), increase in degradation purities, moisture content (K.F.) and % of the active (SS)-(+)-S-adenosyl-L-methionine diastereoisomer; the presence of any degradation products, which can be substantially identified as adenosine and methylthioadenosine and oxidised NADH, expressed as a percentage with respect to the mg of SAMe-toluene sulphonate per tablet and reduced NADH, was further checked by HPLC.

Stress Test

The tablets were prepared in stoppered glass bottles and enclosed in such a way as to reproduce the conditions of final packaging (generally aluminium/aluminium blister).

The samples so prepared were stored for six months in a stove thermostatted to a temperature of 40±2° C. and 75% RH.

Nine samples from three different lots were used for the 400 mg tablets (Examples 1, 2, 3, 4, 5, 6), and each sample from each lot was sampled after 0, 1, 3 and 6 months.

The following tables (14-37) report the results of the stress test.

TABLE 14

Lot 006 - tablets of 400 mg ion/tablet (Example 1)

| Lot (T/t)[1] | Moisture content % (K. Fischer) | S,S % | AD[2] (%) | MTAD[3] (%) | SAMe[4] |
|---|---|---|---|---|---|
| 006 (20/0) | 0.73 | 78.4 | 0.24 | 0.41 | 411.98 |
| 006 (40/1) | 0.59 | 74.2 | 0.36 | 0.63 | 409.45 |
| 006B (40/3) | 0.54 | 71.5 | 0.59 | 0.73 | 409.02 |
| 006C (40/6) | 0.43 | 68.9 | 0.87 | 0.91 | 405.71 |

[1]Temperature (° C.)/time (months);
[2]adenosine;
[3]methylthioadenosine;
[4]SAMe sulphate p-toluene sulphonate (mg/tablet);

TABLE 15

Lot 007 - tablets of 400 mg ion/tablet (Example 1)

| Lot (T/t)[1] | Moisture content % (K. Fischer) | S,S % | AD[2] (%) | MTAD[3] (%) | SAMe[4] |
|---|---|---|---|---|---|
| 007 (20/0) | 0.61 | 79.2 | 0.31 | 0.55 | 412.32 |
| 007A (40/1) | 0.62 | 75.4 | 0.39 | 0.69 | 411.88 |
| 007B (40/3) | 0.57 | 73.1 | 0.52 | 0.72 | 410.67 |
| 007C (40/6) | 0.49 | 70.1 | 0.77 | 0.89 | 408.65 |

[1]Temperature (° C.)/time (months);
[2]adenosine;
[3]methylthioadenosine;
[4]SAMe sulphate p-toluene sulphonate (mg/tablet);

TABLE 16

Lot 008 - tablets of 400 mg ion/tablet (Example 1)

| Lot (T/t)[1] | Moisture content % (K. Fischer) | S,S % | AD[2] (%) | MTAD[3] (%) | SAMe[4] |
|---|---|---|---|---|---|
| 008 (20/0) | 0.81 | 77.9 | 0.34 | 0.49 | 408.54 |
| 008A (40/1) | 0.76 | 73.4 | 0.53 | 0.59 | 407.58 |
| 008B (40/3) | 0.61 | 71.1 | 0.74 | 0.74 | 407.04 |
| 008C (40/6) | 0.55 | 68.8 | 0.88 | 0.84 | 404.21 |

[1]Temperature (° C.)/time (months);
[2]adenosine;
[3]methylthioadenosine;
[4]SAMe sulphate p-toluene sulphonate (mg/tablet);

TABLE 17

Lot 009 - tablets of 400 mg ion/tablet (EXAMPLE 2)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 009 (20/0) | 0.54 | 80.3 | 0.34 | 0.33 | 412.13 | 2.02 |
| 009A (40/1) | 0.50 | 77.4 | 0.39 | 0.45 | 410.54 | 2.01 |
| 009B (40/3) | 0.43 | 72.5 | 0.54 | 0.67 | 410.01 | 2.00 |
| 009C (40/6) | 0.32 | 70.3 | 0.84 | 0.93 | 408.44 | 1.98 |

[1]Temperature (° C.)/time (months);
[2]adenosine;
[3]methylthioadenosine;
[4]SAMe sulphate p-toluene sulphonate (mg/tablet);

TABLE 18

Lot 010 - tablets of 400 mg ion/tablet (EXAMPLE 2)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 010 (20/0) | 0.61 | 80.0 | 0.52 | 0.53 | 410.54 | 2.03 |
| 010A (40/1) | 0.57 | 75.4 | 0.55 | 0.58 | 408.65 | 2.03 |
| 010B (40/3) | 0.51 | 72.3 | 0.67 | 0.69 | 408.56 | 2.00 |
| 010C (40/6) | 0.48 | 70.0 | 0.86 | 0.98 | 406.98 | 1.95 |

[1]Temperature (° C.)/time (months);
[2]adenosine;
[3]methylthioadenosine;
[4]SAMe sulphate p-toluene sulphonate (mg/tablet);

TABLE 19

Lot 011 - tablets of 400 mg ion/tablet (EXAMPLE 2)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 011 (20/0) | 0.75 | 78.3 | 0.24 | 0.34 | 412.21 | 2.00 |
| 011A (40/1) | 0.55 | 75.8 | 0.35 | 0.55 | 410.29 | 2.02 |
| 011B (40/3) | 0.50 | 73.1 | 0.44 | 0.77 | 409.65 | 1.98 |
| 011C (40/6) | 0.47 | 71.3 | 0.75 | 0.97 | 407.65 | 1.95 |

[1]Temperature (° C.)/time (months);
[2]adenosine;
[3]methylthioadenosine;
[4]SAMe sulphate p-toluene sulphonate (mg/tablet);

TABLE 20

Lot 012 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 012 (20/0) | 0.66 | 80.3 | 0.34 | 0.54 | 414.43 | 205.65 |
| 003A (40/1) | 0.61 | 75.4 | 0.43 | 0.66 | 413.43 | 203.54 |
| 012B (40/3) | 0.58 | 72.2 | 0.54 | 0.76 | 411.32 | 203.32 |
| 012C (40/6) | 0.43 | 70.2 | 0.64 | 0.89 | 410.98 | 202.46 |

[1]Temperature (° C.)/time (months);
[2]adenosine;
[3]methylthioadenosine;
[4]SAMe sulphate p-toluene sulphonate (mg/tablet);

TABLE 21

Lot 013 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 013 (20/0) | 0.73 | 79.5 | 0.25 | 0.53 | 412.45 | 203.01 |
| 003A (40/1) | 0.64 | 76.1 | 0.38 | 0.64 | 412.01 | 202.83 |

TABLE 21-continued

Lot 013 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 013B (40/3) | 0.55 | 72.5 | 0.65 | 0.72 | 410.52 | 202.01 |
| 013C (40/6) | 0.47 | 69.9 | 0.79 | 0.96 | 409.74 | 201.21 |

[1]Temperature (° C.)/time (months);
[2]adenosine;
[3]methylthioadenosine;
[4]SAMe sulphate p-toluene sulphonate (mg/tablet);

TABLE 22

Lot 014 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 014 (20/0) | 0.62 | 79.2 | 0.35 | 0.44 | 412.22 | 202.01 |
| 003A (40/1) | 0.60 | 76.4 | 0.45 | 0.55 | 411.01 | 201.43 |
| 014B (40/3) | 0.57 | 72.9 | 0.67 | 0.76 | 410.52 | 200.01 |
| 014C (40/6) | 0.47 | 70.7 | 0.85 | 0.93 | 409.44 | 198.21 |

[1]Temperature (° C.)/time (months);
[2]adenosine;
[3]methylthioadenosine;
[4]SAMe sulphate p-toluene sulphonate (mg/tablet);

TABLE 23

Lot 015 - tablets of 400 mg ion/tablet (Example 4)

| Lot (T/t)[1] | Moisture content % (K. Fischer) | S,S % | AD[2] (%) | MTAD[3] (%) | SAMe[4] |
|---|---|---|---|---|---|
| 018 (20/0) | 0.63 | 79.4 | 0.43 | 0.52 | 412.54 |
| 018A (40/1) | 0.52 | 74.7 | 0.44 | 0.69 | 411.58 |
| 018B (40/3) | 0.41 | 71.5 | 0.58 | 0.78 | 49.78 |
| 018C (40/6) | 0.31 | 68.9 | 0.72 | 0.99 | 407.75 |

[1]Temperature (° C.)/time (months);
[2]adenosine;
[3]methylthioadenosine;
[4]SAMe sulphate p-toluene sulphonate (mg/tablet);

TABLE 24

Lot 016 - tablets of 400 mg ion/tablet (Example 4)

| Lot (T/t)[1] | Moisture content % (K. Fischer) | S,S % | AD[2] (%) | MTAD[3] (%) | SAMe[4] |
|---|---|---|---|---|---|
| 016 (20/0) | 0.56 | 79.2 | 0.33 | 0.49 | 410.54 |
| 001A (40/1) | 0.46 | 75.9 | 0.39 | 0.67 | 410.11 |
| 016B (40/3) | 0.42 | 72.9 | 0.50 | 0.69 | 409.67 |
| 016C (40/6) | 0.39 | 70.7 | 0.86 | 0.87 | 408.65 |

[1]Temperature (° C.)/time (months);
[2]adenosine;
[3]methylthioadenosine;
[4]SAMe sulphate p-toluene sulphonate (mg/tablet);

TABLE 25

Lot 017 - tablets of 400 mg ion/tablet (Example 4)

| Lot (T/t)[1] | Moisture content % (K. Fischer) | S,S % | AD[2] (%) | MTAD[3] (%) | SAMe[4] |
|---|---|---|---|---|---|
| 017 (20/0) | 0.69 | 78.9 | 0.35 | 0.49 | 413.54 |
| 017A (40/1) | 0.59 | 75.4 | 0.45 | 0.69 | 412.58 |
| 017B (40/3) | 0.56 | 72.9 | 0.59 | 0.79 | 409.02 |
| 017C (40/6) | 0.49 | 71.7 | 0.87 | 0.96 | 407.59 |

[1]Temperature (° C.)/time (months);
[2]adenosine;
[3]methylthioadenosine;
[4]SAMe sulphate p-toluene sulphonate (mg/tablet);

TABLE 26

Lot 018 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 018 (20/0) | 0.69 | 80.4 | 0.29 | 0.36 | 412.45 | 3.13 |
| 018A (40/1) | 0.56 | 75.7 | 0.35 | 0.58 | 411.98 | 3.04 |
| 018B (40/3) | 0.50 | 73.2 | 0.54 | 0.87 | 410.71 | 3.01 |
| 018C (40/6) | 0.38 | 70.3 | 0.66 | 1.05 | 407.37 | 3.09 |

[1]Temperature (° C.)/time (months);
[2]adenosine;
[3]methylthioadenosine;
[4]SAMe sulphate p-toluene sulphonate (mg/tablet);

TABLE 27

Lot 019 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 019 (20/0) | 0.59 | 80.1 | 0.55 | 0.33 | 410.00 | 3.10 |
| 019A (40/1) | 0.53 | 75.4 | 0.65 | 0.45 | 410.02 | 3.03 |

TABLE 27-continued

Lot 019 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 019B (40/3) | 0.45 | 72.8 | 0.87 | 0.61 | 408.43 | 3.06 |
| 019C (40/6) | 0.37 | 69.6 | 1.01 | 0.79 | 40627 | 3.07 |

[1]Temperature (° C.)/time (months);
[2]adenosine;
[3]methylthioadenosine;
[4]SAMe sulphate p-toluene sulphonate (mg/tablet);

TABLE 28

Lot 020 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 020 (20/0) | 0.49 | 80.8 | 0.23 | 0.33 | 414.89 | 3.00 |
| 020A (40/1) | 0.50 | 75.8 | 0.37 | 0.51 | 412.29 | 2.89 |
| 020B (40/3) | 0.37 | 72.3 | 0.51 | 0.63 | 409.76 | 2.98 |
| 020C (40/6) | 0.28 | 69.1 | 0.63 | 0.87 | 408.63 | 2.78 |

[1]Temperature (° C.)/time (months);
[2]adenosine;
[3]methylthioadenosine;
[4]SAMe sulphate p-toluene sulphonate (mg/tablet);

TABLE 29

Lot 021 - tablets of 400 mg ion/tablet (Example 6)

| Lot (T/t)[1] | Moisture content % (K. Fischer) | S,S % | AD[2] (%) | MTAD[3] (%) | SAMe[4] | Folic acid mg | L-mela-tonin mg |
|---|---|---|---|---|---|---|---|
| 021 (20/0) | 0.65 | 78.9 | 0.21 | 0.49 | 415.12 | 3.19 | 2.11 |
| 021A (40/1) | 0.53 | 76.1 | 0.34 | 0.57 | 414.21 | 3.23 | 2.02 |
| 021B (40/3) | 0.41 | 72.1 | 0.50 | 0.63 | 413.34 | 3.03 | 2.04 |
| 021C (40/6) | 0.26 | 69.0 | 0.81 | 0.94 | 412.21 | 3.00 | 2.01 |

[1]Temperature (° C.)/time (months);
[2]adenosine;
[3]methylthioadenosine;
[4]SAMe sulphate p-toluene sulphonate (mg/tablet);

TABLE 30

Lot 022 - tablets of 400 mg ion/tablet (Example 6)

| Lot (T/t)[1] | Moisture content % (K. Fischer) | S,S % | AD[2] (%) | MTAD[3] (%) | SAMe[4] | Folic acid mg | L-mela-tonin mg |
|---|---|---|---|---|---|---|---|
| 022 (20/0) | 0.76 | 80.2 | 0.25 | 0.42 | 412.34 | 3.32 | 2.11 |
| 022A (40/1) | 0.64 | 75.9 | 0.27 | 0.54 | 411.21 | 3.23 | 2.10 |

TABLE 30-continued

Lot 022 - tablets of 400 mg ion/tablet (Example 6)

| Lot (T/t)[1] | Moisture content % (K. Fischer) | S,S % | AD[2] (%) | MTAD[3] (%) | SAMe[4] | Folic acid mg | L-mela-tonin mg |
|---|---|---|---|---|---|---|---|
| 022B (40/3) | 0.59 | 72.4 | 0.43 | 0.77 | 410.12 | 3.12 | 2.09 |
| 022C (40/6) | 0.46 | 70.1 | 0.55 | 0.90 | 408.91 | 3.08 | 2.05 |

[1]Temperature (° C.)/time (months);
[2]adenosine;
[3]methylthioadenosine;
[4]SAMe sulphate p-toluene sulphonate (mg/tablet);

TABLE 31

Lot 023 - tablets of 400 mg ion/tablet (Example 6)

| Lot (T/t)[1] | Moisture content % (K. Fischer) | S,S % | AD[2] (%) | MTAD[3] (%) | SAMe[4] | Folic acid mg | L-melatonin mg |
|---|---|---|---|---|---|---|---|
| 023 (20/0) | 0.53 | 81.0 | 0.22 | 0.47 | 411.87 | 3.05 | 2.13 |
| 023A (40/1) | 0.50 | 76.0 | 0.33 | 0.69 | 409.27 | 3.03 | 2.12 |
| 023B (40/3) | 0.41 | 73.7 | 0.55 | 0.73 | 405.34 | 3.08 | 2.07 |
| 023C (40/6) | 0.29 | 69.9 | 0.74 | 0.87 | 404.71 | 3.03 | 2.04 |

[1]Temperature (° C.)/time (months);
[2]adenosine;
[3]methylthioadenosine;
[4]SAMe sulphate p-toluene sulphonate (mg/tablet);

TABLE 32

Lot 001 - tablets of 5.5 mg (Example 7)

| Lot (T/t)[1] | Moisture content % (K. Fischer) | NAD[2] (%) | NADH[3] |
|---|---|---|---|
| 001 (20/0) | 3.30 | 1.41 | 5.43 |
| 001A (40/1) | 3.89 | 2.03 | 4.98 |
| 001B (40/3) | 3.84 | 2.43 | 3.21 |
| 001C (40/6) | 3.63 | 3.61 | 2.21 |

[1]Temperature (° C.)/time (months);
[2]Oxidised NADH;
[3]NADH sodium salt (mg/tablet);

TABLE 33

Lot 002 - tablets of 5.5 mg (Example 7)

| Lot (T/t)[1] | Moisture content % (K. Fischer) | NAD[2] (%) | NADH[3] |
|---|---|---|---|
| 002 (20/0) | 3.10 | 1.55 | 5.23 |
| 002A (40/1) | 3.87 | 2.22 | 4.34 |

TABLE 33-continued

Lot 002 - tablets of 5.5 mg (Example 7)

| Lot (T/t)[1] | Moisture content % (K. Fischer) | NAD[2] (%) | NADH[3] |
|---|---|---|---|
| 002B (40/3) | 3.99 | 2.67 | 3.00 |
| 002C (40/6) | 3.77 | 3.89 | 2.02 |

[1]Temperature (° C.)/time (months);
[2]Oxidised NADH;
[3]NADH sodium salt (mg/tablet);

TABLE 34

Lot 003 - tablets of 5.5 mg (Example 7)

| Lot (T/t)[1] | Moisture content % (K. Fischer) | NAD[2] (%) | NADH[3] |
|---|---|---|---|
| 003 (20/0) | 3.90 | 1.21 | 5.33 |
| 003A (40/1) | 3.65 | 2.23 | 4.58 |
| 003B (40/3) | 3.44 | 2.5 | 3.31 |
| 003C (40/6) | 3.93 | 3.81 | 2.51 |

[1]Temperature (° C.)/time (months);
[2]Oxidised NADH;
[3]NADH sodium salt (mg/tablet);

TABLE 35

Lot 001 - tablets of 5.5 mg (Example 8)

| Lot (T/t)[1] | Moisture content % (K. Fischer) | NAD[2] (%) | NADH[3] |
|---|---|---|---|
| 001 (20/0) | 2.10 | 1.31 | 5.40 |
| 001A (40/1) | 1.99 | 1.43 | 5.32 |
| 001B (40/3) | 1.80 | 1.53 | 5.21 |
| 001C (40/6) | 1.33 | 1.81 | 5.00 |

[1]Temperature (° C.)/time (months);
[2]Oxidised NADH;
[3]NADH sodium salt (mg/tablet);

TABLE 36

Lot 002 - tablets of 5.5 mg (Example 8)

| Lot (T/t)[1] | Moisture content % (K. Fischer) | NAD[2] (%) | NADH[3] |
|---|---|---|---|
| 002 (20/0) | 2.00 | 1.23 | 5.52 |
| 002A (40/1) | 1.36 | 1.32 | 5.34 |
| 002B (40/3) | 1.45 | 1.57 | 5.12 |
| 002C (40/6) | 1.27 | 1.99 | 4.89 |

[1]Temperature (° C.)/time (months);
[2]Oxidised NADH;
[3]NADH sodium salt (mg/tablet);

TABLE 37

Lot 003 - tablets of 5.5 mg (Example 8)

| Lot (T/t)[1] | Moisture content % (K. Fischer) | NAD[2] (%) | NADH[3] |
|---|---|---|---|
| 003 (20/0) | 2.90 | 1.29 | 5.35 |
| 003A (40/1) | 1.65 | 1.56 | 5.21 |
| 003B (40/3) | 1.44 | 1.99 | 4.98 |
| 003C (40/6) | 1.12 | 2.31 | 4.67 |

[1]Temperature (° C.)/time (months);
[2]Oxidised NADH;
[3]NADH sodium salt (mg/tablet);

From the stability data at 40° C. and 75% RH (STRESS TEST) it will be seen that all the lots examined after six months had suffered degradation equal to approximately 2.5% of both SAMe and the other active ingredients with a reduction of approximately 10% in the active (SS)-(+)-S-adenosyl-L-methionine diastereoisomers;

From the stability data at 40° C. and 75% RH (STRESS TEST) it will be seen that all the lots of NADH examined containing calcium oxide had undergone approximately 50% less degradation than the lots without calcium oxide after six months.

Shelf Life

The tablets were packed in stoppered glass bottles and enclosed in such a way as to reproduce the conditions of final packaging (generally aluminium/aluminium blister).

The samples were selected in the same way and in the same quantities as described for the stress test and kept in an environment thermostatted to a temperature of 25±2° C. and a humidity of 60% RH.

Nine samples originating from three different lots were used for the 400 mg tablets (Examples 1, 2, 3, 4, 5, 6, 7, 8) and each sample from each lot was sampled after 0, 3, 6, 12 months.

The following tables (38-61) show the results for SHELF LIFE.

TABLE 38

Lot 024 - tablets of 400 mg ion/tablet (Example 1)

| Lot (T/t)[1] | Moisture content % (K. Fischer) | S,S % | AD[2] (%) | MTAD[3] (%) | SAMe[4] |
|---|---|---|---|---|---|
| 024 (20/0) | 0.65 | 79.4 | 0.32 | 0.28 | 413.48 |
| 024A (25/3) | 0.56 | 75.3 | 0.44 | 0.34 | 413.23 |
| 024B (25/6) | 0.52 | 72.5 | 0.59 | 0.65 | 411.89 |
| 024C (25/12) | 0.44 | 69.9 | 0.83 | 0.79 | 409.76 |

[1]Temperature (° C.)/time (months);
[2]adenosine;
[3]methylthioadenosine;
[4]SAMe sulphate p-toluene sulphonate (mg/tablet);

TABLE 39

Lot 025 - tablets of 400 mg ion/tablet (Example 1)

| Lot (T/t)[1] | Moisture content % (K. Fischer) | S,S % | AD[2] (%) | MTAD[3] (%) | SAMe[4] |
|---|---|---|---|---|---|
| 006 (20/0) | 0.69 | 78.9 | 0.27 | 0.46 | 410.67 |
| 025 (25/3) | 0.65 | 74.6 | 0.39 | 0.67 | 408.78 |
| 025B (25/6) | 0.56 | 73.5 | 0.65 | 0.74 | 409.02 |
| 025C (25/12) | 0.34 | 70.4 | 0.79 | 0.89 | 405.32 |

[1]Temperature (° C.)/time (months);
[2]adenosine;
[3]methylthioadenosine;
[4]SAMe sulphate p-toluene sulphonate (mg/tablet);

TABLE 40

Lot 026 - tablets of 400 mg ion/tablet (Example 1)

| Lot (T/t)[1] | Moisture content % (K. Fischer) | S,S % | AD[2] (%) | MTAD[3] (%) | SAMe[4] |
|---|---|---|---|---|---|
| 026 (20/0) | 0.78 | 78.7 | 0.20 | 0.47 | 411.65 |
| 006 (25/3) | 0.65 | 74.9 | 0.39 | 0.60 | 409.43 |
| 026B (25/6) | 0.54 | 72.5 | 0.69 | 0.70 | 408.02 |
| 026C (25/12) | 0.48 | 68.45 | 0.88 | 0.94 | 404.43 |

[1]Temperature (° C.)/time (months);
[2]adenosine;
[3]methylthioadenosine;
[4]SAMe sulphate p-toluene sulphonate (mg/tablet);

TABLE 41

Lot 027 - tablets of 400 mg ion/tablet (Example 2)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 027 (20/0) | 0.70 | 80.0 | 0.41 | 0.20 | 410.24 | 2.12 |
| 010A (25/3) | 0.64 | 75.7 | 0.54 | 0.47 | 408.65 | 2.04 |
| 027B (25/6) | 0.55 | 72.7 | 0.69 | 0.58 | 405.56 | 2.05 |
| 027C (25/12) | 0.43 | 70.4 | 0.83 | 0.85 | 406.58 | 1.99 |

[1]Temperature (° C.)/time (months);
[2]adenosine;
[3]methylthioadenosine;
[4]SAMe sulphate p-toluene sulphonate (mg/tablet);

TABLE 42

Lot 028 - tablets of 400 mg ion/tablet (Example 2)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 010 (20/0) | 0.64 | 80.4 | 0.33 | 0.35 | 413.44 | 2.07 |
| 028A (25/3) | 0.54 | 76.73 | 0.45 | 0.54 | 412.35 | 2.09 |
| 028B (25/6) | 0.50 | 73.9 | 0.67 | 0.56 | 408.46 | 2.04 |
| 028C (25/12) | 0.37 | 73.0 | 0.85 | 0.67 | 406.58 | 2.02 |

[1]Temperature (° C.)/time (months);
[2]adenosine;
[3]methylthioadenosine;
[4]SAMe sulphate p-toluene sulphonate (mg/tablet);

TABLE 43

Lot 029 - tablets of 400 mg ion/tablet (Example 2)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 029 (20/0) | 0.64 | 78.7 | 0.33 | 0.45 | 408.43 | 2.13 |
| 029A (25/3) | 0.57 | 75.3 | 0.34 | 0.54 | 407.55 | 2.12 |
| 029B (25/6) | 0.51 | 72.5 | 0.54 | 0.56 | 404.45 | 2.05 |
| 029C (25/12) | 0.39 | 71.2 | 0.67 | 0.76 | 403.23 | 1.99 |

[1]Temperature (° C.)/time (months);
[2]adenosine;
[3]methylthioadenosine;
[4]SAMe sulphate p-toluene sulphonate (mg/tablet);

TABLE 44

Lot 030 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 030 (20/0) | 0.71 | 79.76 | 0.22 | 0.34 | 413.49 | 209.35 |
| 030A (25/3) | 0.61 | 74.7 | 0.33 | 0.46 | 412.33 | 203.54 |
| 030B (25/6) | 0.55 | 73.2 | 0.51 | 0.66 | 410.32 | 202.32 |
| 030C (25/12) | 0.49 | 71.4 | 0.69 | 0.79 | 404.98 | 200.32 |

[1]Temperature (° C.)/time (months);
[2]adenosine;
[3]methylthioadenosine;
[4]SAMe sulphate p-toluene sulphonate (mg/tablet);

TABLE 45

Lot 031 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 031 (20/0) | 0.62 | 80.4 | 0.37 | 0.43 | 412.43 | 205.21 |
| 031A (25/3) | 0.56 | 74.4 | 0.40 | 0.54 | 410.45 | 204.54 |

TABLE 45-continued

Lot 031 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 031B (25/6) | 0.58 | 71.2 | 0.50 | 0.65 | 407.78 | 203.23 |
| 031C (25/12) | 0.49 | 68.5 | 0.61 | 0.79 | 407.21 | 201.34 |

[1]Temperature (° C.)/time (months);
[2]adenosine;
[3]methylthioadenosine;
[4]SAMe sulphate p-toluene sulphonate (mg/tablet);

TABLE 46

Lot 032 - tablets of 400 mg ion/tablet (Example 3)

| Lot (T/t)[1] | Moisture content % (K. Fischer) | S,S % | AD[2] (%) | MTAD[3] (%) | SAMe[4] | L-theanine |
|---|---|---|---|---|---|---|
| 032 (20/0) | 0.63 | 81.5 | 0.44 | 0.24 | 409.99 | 203.65 |
| 032A (25/3) | 0.65 | 75.5 | 0.43 | 0.46 | 406.78 | 202.45 |
| 032B (25/6) | 0.59 | 73.4 | 0.64 | 0.56 | 406.54 | 203.00 |
| 032C (25/12) | 0.50 | 70.0 | 0.84 | 0.75 | 404.21 | 201.23 |

[1]Temperature (° C.)/time (months);
[2]adenosine;
[3]methylthioadenosine;
[4]SAMe sulphate p-toluene sulphonate (mg/tablet);

TABLE 47

Lot 033 - tablets of 400 mg ion/tablet (Example 4)

| Lot (T/t)[1] | Moisture content % (K. Fischer) | S,S % | AD[2] (%) | MTAD[3] (%) | SAMe[4] |
|---|---|---|---|---|---|
| 033 (20/0) | 0.74 | 79.9 | 0.39 | 0.29 | 411.23 |
| 033A (25/3) | 0.64 | 74.4 | 0.44 | 0.38 | 409.45 |
| 033B (25/6) | 0.59 | 73.5 | 0.63 | 0.57 | 406.02 |
| 033C (25/12) | 0.34 | 70.6 | 0.88 | 0.89 | 404.23 |

[1]Temperature (° C.)/time (months);
[2]adenosine;
[3]methylthioadenosine;
[4]SAMe sulphate p-toluene sulphonate (mg/tablet);

TABLE 48

Lot 034 - tablets of 400 mg ion/tablet (Example 4)

| Lot (T/t)[1] | Moisture content % (K. Fischer) | S,S % | AD[2] (%) | MTAD[3] (%) | SAMe[4] |
|---|---|---|---|---|---|
| 034 (20/0) | 0.59 | 78.3 | 0.25 | 0.39 | 410.23 |
| 034A (25/3) | 0.60 | 73.4 | 0.35 | 0.57 | 408.58 |
| 034B (25/6) | 0.53 | 70.9 | 0.49 | 0.88 | 404.32 |
| 034C (25/12) | 0.39 | 68.5 | 0.68 | 0.90 | 402.12 |

[1]Temperature (° C.)/time (months);
[2]adenosine;
[3]methylthioadenosine;
[4]SAMe sulphate p-toluene sulphonate (mg/tablet);

TABLE 49

Lot 035 - tablets of 400 mg ion/tablet (Example 4)

| Lot (T/t)[1] | Moisture content % (K. Fischer) | S,S % | AD[2] (%) | MTAD[3] (%) | SAMe[4] |
|---|---|---|---|---|---|
| 035 (20/0) | 0.59 | 78.7 | 0.38 | 0.39 | 408.56 |
| 035A (25/3) | 0.49 | 74.9 | 0.49 | 0.57 | 409.65 |
| 035B (25/6) | 0.50 | 72.0 | 0.65 | 0.68 | 404.73 |
| 035C (25/12) | 0.36 | 70.2 | 0.97 | 0.87 | 402.12 |

[1]Temperature (° C.)/time (months);
[2]adenosine;
[3]methylthioadenosine;
[4]SAMe sulphate p-toluene sulphonate (mg/tablet);

TABLE 50

Lot 036 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 036 (20/0) | 0.70 | 80.4 | 0.47 | 0.37 | 413.00 | 3.05 |
| 036A (25/3) | 0.58 | 74.4 | 0.56 | 0.40 | 410.45 | 3.03 |
| 036B (25/6) | 0.42 | 72.0 | 0.78 | 0.66 | 408.99 | 3.06 |
| 036C (25/12) | 0.39 | 69.8 | 0.89 | 0.72 | 404.67 | 3.01 |

[1]Temperature (° C.)/time (months);
[2]adenosine;
[3]methylthioadenosine;
[4]SAMe sulphate p-toluene sulphonate (mg/tablet);

TABLE 51

Lot 037 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 037 (20/0) | 0.69 | 78.7 | 0.49 | 0.39 | 411.30 | 3.05 |
| 037A (25/3) | 0.63 | 74.5 | 0.64 | 0.55 | 408.57 | 3.01 |

TABLE 51-continued

Lot 037 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 037B (25/6) | 0.59 | 71.8 | 0.81 | 0.67 | 405.98 | 3.00 |
| 037C (25/12) | 0.48 | 69.2 | 1.00 | 0.89 | 402.56 | 2.89 |

[1]Temperature (° C.)/time (months);
[2]adenosine;
[3]methylthioadenosine;
[4]SAMe sulphate p-toluene sulphonate (mg/tablet);

TABLE 52

Lot 038 - tablets of 400 mg ion/tablet (Example 5)

| Lot (T/t)[1] | Moisture content % (K. Fischer) | S,S % | AD[2] (%) | MTAD[3] (%) | SAMe[4] | Folic acid mg |
|---|---|---|---|---|---|---|
| 038 (20/0) | 0.70 | 81.2 | 0.52 | 0.31 | 410.99 | 3.11 |
| 038A (25/3) | 0.63 | 75.4 | 0.60 | 0.43 | 407.32 | 3.08 |
| 038B (25/6) | 0.58 | 73.2 | 0.76 | 0.68 | 405.89 | 3.03 |
| 038C (25/12) | 0.49 | 70.6 | 0.80 | 0.93 | 401.34 | 3.01 |

[1]Temperature (° C.)/time (months);
[2]adenosine;
[3]methylthioadenosine;
[4]SAMe sulphate p-toluene sulphonate (mg/tablet);

TABLE 53

Lot 039 - tablets of 400 mg ion/tablet (Example 6)

| Lot (T/t)[1] | Moisture content % (K. Fischer) | S,S % | AD[2] (%) | MTAD[3] (%) | SAMe[4] | Folic acid mg | L-melatonin mg |
|---|---|---|---|---|---|---|---|
| 039 (20/0) | 0.63 | 81.4 | 0.29 | 0.43 | 410.43 | 3.03 | 2.06 |
| 039A (25/3) | 0.53 | 74.7 | 0.39 | 0.65 | 406.89 | 3.05 | 2.07 |
| 039B (25/6) | 0.57 | 72.7 | 0.58 | 0.79 | 403.69 | 3.00 | 2.03 |
| 039C (25/12) | 0.42 | 70.9 | 0.79 | 0.89 | 401.34 | 2.89 | 2.02 |

[1]Temperature (° C.)/time (months);
[2]adenosine;
[3]methylthioadenosine;
[4]SAMe sulphate p-toluene sulphonate (mg/tablet);

TABLE 54

Lot 040 - tablets of 400 mg ion/tablet (Example 6)

| Lot (T/t)[1] | Moisture content % (K. Fischer) | S,S % | AD[2] (%) | MTAD[3] (%) | SAMe[4] | Folic acid mg | L-melatonin mg |
|---|---|---|---|---|---|---|---|
| 040 (20/0) | 0.63 | 78.8 | 0.35 | 0.40 | 408.88 | 3.10 | 2.05 |
| 040A (25/3) | 0.58 | 74.5 | 0.45 | 0.67 | 404.47 | 3.07 | 2.02 |
| 040B (25/6) | 0.48 | 72.5 | 0.60 | 0.70 | 403.34 | 3.03 | 2.07 |
| 040C (25/12) | 0.37 | 69.3 | 0.78 | 0.89 | 400.45 | 3.00 | 2.00 |

[1]Temperature (° C.)/time (months);
[2]adenosine;
[3]methylthioadenosine;
[4]SAMe sulphate p-toluene sulphonate (mg/tablet);

TABLE 55

Lot 041 - tablets of 400 mg ion/tablet (Example 6)

| Lot (T/t)[1] | Moisture content % (K. Fischer) | S,S % | AD[2] (%) | MTAD[3] (%) | SAMe[4] | Folic acid mg | L-melatonin mg |
|---|---|---|---|---|---|---|---|
| 041 (20/0) | 0.73 | 81.6 | 0.42 | 0.38 | 410.48 | 3.15 | 2.10 |
| 023A (25/3) | 0.70 | 75.3 | 0.43 | 0.49 | 407.56 | 3.09 | 2.12 |
| 041B (25/6) | 0.58 | 72.4 | 0.58 | 0.70 | 406.65 | 3.08 | 2.08 |
| 041C (25/12) | 0.49 | 70.4 | 0.73 | 0.88 | 402.39 | 3.05 | 2.03 |

[1]Temperature (° C.)/time (months);
[2]adenosine;
[3]methylthioadenosine;
[4]SAMe sulphate p-toluene sulphonate (mg/tablet);

TABLE 56

Lot 001 - tablets of 5.5 mg (Example 7)

| Lot (T/t)[1] | Moisture content % (K. Fischer) | NAD[2] (%) | NADH[3] |
|---|---|---|---|
| 001 (20/0) | 3.30 | 1.41 | 5.43 |
| 001A (25/1) | 3.34 | 1.53 | 5.23 |
| 001B (25/3) | 3.54 | 1.73 | 5.11 |
| 001C (25/6) | 3.23 | 2.21 | 4.65 |

[1]Temperature (° C.)/time (months);
[2]Oxidised NADH;
[3]NADH sodium salt (mg/tablet);

TABLE 57

Lot 002 - tablets of 5.5 mg (Example 7)

| Lot (T/t)[1] | Moisture content % (K. Fischer) | NAD[2] (%) | NADH[3] |
|---|---|---|---|
| 002 (20/0) | 3.10 | 1.55 | 5.23 |
| 002A (25/1) | 3.02 | 1.65 | 5.02 |

TABLE 57-continued

Lot 002 - tablets of 5.5 mg (Example 7)

| Lot (T/t)[1] | Moisture content % (K. Fischer) | NAD[2] (%) | NADH[3] |
|---|---|---|---|
| 002B (25/3) | 3.00 | 1.87 | 4.70 |
| 002C (25/6) | 3.17 | 2.79 | 4.45 |

[1]Temperature (° C.)/time (months);
[2]Oxidised NADH;
[3]NADH sodium salt (mg/tablet);

TABLE 58

Lot 003 - tablets of 5.5 mg (Example 7)

| Lot (T/t)[1] | Moisture content % (K. Fischer) | NAD[2] (%) | NADH[3] |
|---|---|---|---|
| 003 (20/0) | 3.90 | 1.21 | 5.33 |
| 003A (25/1) | 3.75 | 1.43 | 5.21 |
| 003B (25/3) | 3.84 | 1.50 | 5.11 |
| 003C (25/6) | 3.34 | 2.61 | 4.87 |

[1]Temperature (° C.)/time (months);
[2]Oxidised NADH;
[3]NADH sodium salt (mg/tablet);

TABLE 59

Lot 001 - tablets of 5.5 mg (Example 8)

| Lot (T/t)[1] | Moisture content % (K. Fischer) | NAD[2] (%) | NADH[3] |
|---|---|---|---|
| 001 (20/0) | 2.10 | 1.31 | 5.40 |
| 001A (25/1) | 1.87 | 1.33 | 5.38 |
| 001B (25/3) | 1.89 | 1.43 | 5.31 |
| 001C (25/6) | 1.43 | 1.51 | 5.20 |

[1]Temperature (° C.)/time (months);
[2]Oxidised NADH;
[3]NADH sodium salt (mg/tablet);

TABLE 60

Lot 002 - tablets of 5.5 mg (Example 8)

| Lot (T/t)[1] | Moisture content % (K. Fischer) | NAD[2] (%) | NADH[3] |
|---|---|---|---|
| 002 (20/0) | 2.00 | 1.23 | 5.52 |
| 002A (25/1) | 1.76 | 1.30 | 5.44 |
| 002B (25/3) | 1.85 | 1.47 | 5.42 |
| 002C (25/6) | 1.57 | 1.67 | 5.29 |

[1]Temperature (° C.)/time (months);
[2]Oxidised NADH;
[3]NADH sodium salt (mg/tablet);

TABLE 61

Lot 003 - tablets of 5.5 mg (Example 8)

| Lot (T/t)[1] | Moisture content % (K. Fischer) | NAD[2] (%) | NADH[3] |
|---|---|---|---|
| 003 (20/0) | 2.90 | 1.29 | 5.35 |
| 003A (25/1) | 1.75 | 1.36 | 5.29 |
| 003B (25/3) | 1.84 | 149 | 5.12 |
| 003C (25/6) | 1.62 | 1.78 | 5.07 |

[1]Temperature (° C.)/time (months);
[2]Oxidised NADH;
[3]NADH sodium salt (mg/tablet);

From the stability data at 25° C. and 60% RH (SHELF LIFE) it will be seen that all the lots examined after twelve months had suffered very little degradation of the SAMe with a reduction of approximately 10% in the active (SS)-(+)-S-adenosyl-L-methionine diastereoisomer;

From the stability data at 25° C. and 60% RH (SHELF LIFE) it will be seen that all the lots of NADH examined which contained calcium oxide had undergone approximately 50% less degradation than the lots without calcium oxide after six months.

Comparative Examples

The following three comparative examples reproducing the formulation of examples 1, 2, and 3 without the presence of calcium oxide have been introduced.

Examples

Example 1A

Tablets of 400 mg SAMe Ion/Tablet
Composition Based on SAMe Sulphate p-Toluene Sulphonate

| | |
|---|---|
| A. SAMe sulphate p-toluene sulphonate | 800.00 mg |
| B Calcium oxide absent | 00.00 mg |
| C. Magnesium hydroxide | 150.00 mg |
| D. Saccharose | 100.00 mg |
| E. Calcium carbonate | 80.00 mg |
| F. Magnesium stearate | 20.00 mg |
| G. Malic acid | 40.00 mg |
| E. Hydrogenated fatty acid | 50.00 mg |
| Total weight of core | 1240.00 mg |

-continued

| | |
|---|---|
| F. Hydrogenated vegetable fatty acids | 4.00 mg |
| G. Shellac ® | 30.00 mg |
| H. PVP K 30 | 6.0 mg |
| I. Titanium dioxide | 5.00 mg |
| L. Talc | 10.00 mg |
| M. Triethyl citrate | 5.00 mg |
| N. Curcumin | 0.050 mg |
| Total weight of tablet | 1300.50 mg |

Stability tests on uncoated tablets were performed at only 40° C. and 75% RH for six months and for a single lot because this is not a finished product. The samples were stored in alu/alu blisters.

TABLE 9A

Lot 001A - cores of 400 mg ion/tablet (qualitative/quantitative composition in Example 1A)

| Lot (T/t)[1] | Moisture content % (K. Fischer) | S,S % | AD[2] (%) | MTAD[3] (%) | SAMe[4] |
|---|---|---|---|---|---|
| 001 (20/0) | 0.69 | 79.6 | 0.25 | 0.49 | 412.32 |
| 001A (40/1) | 0.66 | 73.2 | 0.65 | 0.97 | 409.23 |
| 001B (40/3) | 0.87 | 63.4 | 1.98 | 3.23 | 386.32 |
| 001C (40/6) | 0.79 | 53.2 | 3.32 | 9.56 | 365.67 |

[1]Temperature (° C.)/time (months);
[2]adenosine;
[3]methylthioadenosine;
[4]SAMe sulphate p-toluene sulphonate (mg/tablet);

The data in Table 9A show that the tablets have non good stability.

Example 2A

Tablets of 400 mg SAMe Ion/Tablet
Compositions Based on SAMe Sulphate p-Toluene Sulphonate

| | |
|---|---|
| A. SAMe sulphate p-toluene sulphonate | 800.00 mg |
| B. L-melatonin | 2.00 mg |
| C Calcium oxide absent | 00.00 mg |
| D. Magnesium hydroxide | 170.00 mg |
| E. Calcium sulphate hemihydrate | 100.00 mg |
| F. Calcium carbonate | 160.00 mg |
| G. Magnesium stearate | 20.00 mg |
| H. Malic acid | 40.00 mg |
| I. Hydrogenated fatty acid | 40.00 mg |
| Total weight of core | 1332.00 mg |
| L. Hydrogenated vegetable fatty acids | 4.00 mg |
| M. Shellac ® | 30.00 mg |
| N. PVP K 30 | 6.0 mg |
| O. Titanium dioxide | 5.00 mg |
| P. Talc | 10.00 mg |
| Q. Triethyl citrate | 5.00 mg |
| R. Curcumin | 0.050 mg |
| Total weight of tablet | 1302.50 mg |

The quantities relate to the preparation of a standard industrial lot of 250.00 kg of tablets.

The tablets were prepared in the manner described in Example 1 using the components and quantities indicated above.

TABLE 10A

Lot 002A - cores of 400 mg/ion/tablet (qualitative/quantitative composition in Example 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 002 (20/0) | 0.87 | 80.0 | 0.34 | 0.69 | 412.21 | 2.00 |
| 002A (40/1) | 0.91 | 66.5 | 0.76 | 1.38 | 403.45 | 2.01 |
| 002B (40/3) | 0.92 | 63.2 | 2.02 | 4.75 | 381.64 | 2.01 |
| 002C (40/6) | 0.90 | 51.0 | 3.79 | 10.73 | 360.32 | 1.98 |

[1]Temperature (° C.)/time (months);
[2]adenosine;
[3]methylthioadenosine;
[4]SAMe sulphate p-toluene sulphonate (mg/tablet);

The data in Table 10A indicate that the tablets have non good stability.

Example 3A

Tablets of 400 mg SAMe Ion/Tablet
Composition Based on SAMe Sulphate p-Toluene Sulphonate

| | |
|---|---|
| A. SAMe sulphate p-toluene sulphonate | 800.00 mg |
| B. L-theanine | 200.00 mg |
| C Calcium oxide absent | 00.00 mg |
| D. Magnesium hydroxide | 170.00 mg |
| E. Xylitol | 50.00 mg |
| F. Calcium carbonate | 100.00 mg |
| G. Microcrystalline cellulose | 60.00 mg |
| H. Magnesium stearate | 20.00 mg |
| I. Malic acid | 40.00 mg |
| L. Hydrogenated fatty acid | 40.00 mg |
| Total weight of core | 1480.00 mg |
| M. Hydrogenated vegetable fatty acids | 4.00 mg |
| N. Shellac ® | 30.00 mg |
| O. PVP K 30 | 6.0 mg |
| P. Titanium dioxide | 5.00 mg |
| Q. Talc | 10.00 mg |
| R. Triethyl citrate | 5.00 mg |
| S. Hydroxypropylmethylcellulose | 10.00 mg |
| T. Curcumin | 0.050 mg |
| Total weight of tablet | 1550.05 mg |

The quantities relate to the preparation of a standard industrial lot of 250.00 kg of tablets.

The tablets were prepared in the manner described in Example 1 using the components and quantities indicated above.

TABLE 11A

Lot 003A - cores of 400 mg ion/tablet (qualitative/quantitative composition in Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 003 (20/0) | 0.98 | 78.2 | 0.34 | 0.74 | 408.39 | 203.53 |
| 003A (40/1) | 0.93 | 72.3 | 0.75 | 1.34 | 399.74 | 202.54 |
| 003B (40/3) | 1.05 | 62.3 | 2.45 | 4.72 | 378.32 | 202.11 |

TABLE 11A-continued

Lot 003A - cores of 400 mg ion/tablet (qualitative/quantitative composition in Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 003C (40/6) | 1.07 | 51.9 | 4.69 | 12.78 | 354.67 | 200.62 |

[1]Temperature (° C.)/time (months);
[2]adenosine;
[3]methylthioadenosine;
[4]SAMe sulphate p-toluene sulphonate (mg/tablet);

The data in Table 11A show that the tablets have non good stability.

Experimental Part

Stability Tests on the Finished Product

Stability at 40° C. 75% RH (STRESS TEST) and at ambient temperature over a long period (SHELF LIFE) for the compositions in Examples 1A, 2A, 3A, obtained according to the process according to the invention were evaluated for changes in appearance (essentially change in colour), titre of SAMe sulphate p-toluene sulphonate, increase in degradation purities, moisture content (K.F.) and % of the active (SS)-(+)-S-adenosyl-L-methionine diastereoisomer; the presence of any degradation products, which can be substantially identified as adenosine and methylthioadenosine, expressed as a percentage with respect to the mg of SAMe-toluene sulphonate per tablet, was further checked by HPLC.

Stress Test

The tablets were prepared in stoppered glass bottles and enclosed in such a way as to reproduce the conditions of final packaging (generally aluminium/aluminium blister).

The samples so prepared were stored for six months in a stove thermostatted to a temperature of 40±2° C. and 75% RH.

Nine samples from three different lots were used for the 400 mg tablets (Examples 1A, 2A, 3A), and each sample from each lot was sampled after 0, 1, 3 and 6 months.

The following tables (14A-22A) report the results of the stress test.

TABLE 14A

Lot 006A - tablets of 400 mg ion/tablet (Example 1A)

| Lot (T/t)[1] | Moisture content % (K. Fischer) | S,S % | AD[2] (%) | MTAD[3] (%) | SAMe[4] |
|---|---|---|---|---|---|
| 006 (20/0) | 0.99 | 78.1 | 0.35 | 0.81 | 410.23 |
| 006 (40/1) | 1.16 | 71.2 | 0.85 | 1.37 | 404.45 |
| 006B (40/3) | 1.18 | 60.1 | 2.54 | 4.63 | 379.34 |
| 006C (40/6) | 1.29 | 50.8 | 4.82 | 11.98 | 350.78 |

[1]Temperature (° C.)/time (months);
[2]adenosine;
[3]methylthioadenosine;
[4]SAMe sulphate p-toluene sulphonate (mg/tablet);

TABLE 15A

Lot 007A - tablets of 400 mg ion/tablet (Example 1A)

| Lot (T/t)[1] | Moisture content % (K. Fischer) | S,S % | AD[2] (%) | MTAD[3] (%) | SAMe[4] |
|---|---|---|---|---|---|
| 007 (20/0) | 1.00 | 77.3 | 0.43 | 0.79 | 411.01 |
| 007A (40/1) | 0.96 | 71.8 | 0.85 | 1.65 | 406.29 |
| 007B (40/3) | 1.09 | 62.0 | 2.33 | 2.98 | 380.11 |
| 007C (40/6) | 1.09 | 52.1 | 4.01 | 10.90 | 355.99 |

[1]Temperature (° C.)/time (months);
[2]adenosine;
[3]methylthioadenosine;
[4]SAMe sulphate p-toluene sulphonate (mg/tablet);

TABLE 16A

Lot 008A - tablets of 400 mg ion/tablet (Example 1A)

| Lot (T/t)[1] | Moisture content % (K. Fischer) | S,S % | AD[2] (%) | MTAD[3] (%) | SAMe[4] |
|---|---|---|---|---|---|
| 008 (20/0) | 1.02 | 75.7 | 0.33 | 0.85 | 410.11 |
| 008A (40/1) | 1.03 | 70.3 | 0.95 | 1.47 | 403.98 |
| 008B (40/3) | 1.23 | 61.4 | 2.98 | 4.45 | 376.29 |
| 008C (40/6) | 1.56 | 51.1 | 5.02 | 13.54 | 345.87 |

[1]Temperature (° C.)/time (months);
[2]adenosine;
[3]methylthioadenosine;
[4]SAMe sulphate p-toluene sulphonate (mg/tablet);

TABLE 17A

Lot 009A - tablets of 400 mg ion/tablet (EXAMPLE 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 009 (20/0) | 0.99 | 78.1 | 0.41 | 0.88 | 409.55 | 2.03 |
| 009A (40/1) | 1.21 | 68.4 | 0.96 | 1.65 | 401.33 | 2.01 |
| 009B (40/3) | 0.98 | 59.8 | 2.23 | 4.45 | 376.64 | 2.11 |
| 009C (40/6) | 1.11 | 52.3 | 3.99 | 11.23 | 351.34 | 1.98 |

[1]Temperature (° C.)/time (months);
[2]adenosine;
[3]methylthioadenosine;
[4]SAMe sulphate p-toluene sulphonate (mg/tablet);

TABLE 18A

Lot 010A - tablets of 400 mg ion/tablet (EXAMPLE 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 010 (20/0) | 0.87 | 77.3 | 0.46 | 0.83 | 409.59 | 2.12 |
| 010A (40/1) | 1.11 | 67.2 | 1.06 | 1.55 | 402.66 | 2.08 |

TABLE 18A-continued

Lot 010A - tablets of 400 mg ion/tablet (EXAMPLE 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 010B (40/3) | 1.18 | 59.4 | 2.55 | 4.67 | 381.23 | 2.01 |
| 010C (40/6) | 1.31 | 51.2 | 3.67 | 10.45 | 367.34 | 2.03 |

[1]Temperature (° C.)/time (months);
[2]adenosine;
[3]methylthioadenosine;
[4]SAMe sulphate p-toluene sulphonate (mg/tablet);

TABLE 19A

Lot 011A - tablets of 400 mg ion/tablet (EXAMPLE 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 011 (20/0) | 1.07 | 76.8 | 0.57 | 0.89 | 409.00 | 2.10 |
| 011A (40/1) | 1.14 | 67.5 | 1.33 | 1.72 | 400.87 | 2.04 |
| 011B (40/3) | 1.23 | 58.9 | 2.87 | 4.87 | 376.29 | 2.04 |
| 011C (40/6) | 1.38 | 53.5 | 4.88 | 11.89 | 362.54 | 2.03 |

[1]Temperature (° C.)/time (months);
[2]adenosine;
[3]methylthioadenosine;
[4]SAMe sulphate p-toluene sulphonate (mg/tablet);

TABLE 20A

Lot 012A - tablets of 400 mg ion/tablet (Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 012 (20/0) | 1.21 | 76.7 | 0.36 | 0.84 | 407.00 | 202.72 |
| 003A (40/1) | 1.18 | 69.1 | 0.88 | 1.54 | 397.64 | 201.39 |
| 012B (40/3) | 1.35 | 63.4 | 2.75 | 4.87 | 379.98 | 200.41 |
| 012C (40/6) | 1.57 | 52.7 | 4.43 | 11.68 | 361.82 | 198.42 |

[1]Temperature (° C.)/time (months);
[2]adenosine;
[3]methylthioadenosine;
[4]SAMe sulphate p-toluene sulphonate (mg/tablet);

TABLE 21A

Lot 013A - tablets of 400 mg ion/tablet (Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 013 (20/0) | 1.04 | 77.3 | 0.39 | 0.89 | 408.34 | 203.56 |
| 003A (40/1) | 1.07 | 68.4 | 0.85 | 1.57 | 399.84 | 202.49 |
| 013B (40/3) | 1.24 | 62.3 | 2.45 | 4.38 | 383.67 | 201.83 |
| 013C (40/6) | 1.37 | 51.9 | 4.23 | 9.87 | 370.52 | 199.27 |

[1]Temperature (° C.)/time (months);
[2]adenosine;
[3]methylthioadenosine;
[4]SAMe sulphate p-toluene sulphonate (mg/tablet);

TABLE 22A

Lot 014A - tablets of 400 mg ion/tablet (Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 014 (20/0) | 1.00 | 75.3 | 0.53 | 0.92 | 406.23 | 205.52 |
| 003A (40/1) | 1.02 | 67.3 | 1.03 | 1.71 | 395.29 | 203.67 |
| 014B (40/3) | 1.13 | 61.2 | 2.82 | 3.89 | 371.28 | 202.61 |
| 014C (40/6) | 1.29 | 50.6 | 4.65 | 10.21 | 356.72 | 201.56 |

[1]Temperature (° C.)/time (months);
[2]adenosine;
[3]methylthioadenosine;
[4]SAMe sulphate p-toluene sulphonate (mg/tablet);

Shelf Life

The tablets were packed in stoppered glass bottles and enclosed in such a way as to reproduce the conditions of final packaging (generally aluminium/aluminium blister).

The samples were selected in the same way and in the same quantities as described for the stress test and kept in an environment thermostatted to a temperature of 25±2° C. and a humidity of 60% RH.

Nine samples originating from three different lots were used for the 400 mg tablets (Examples 1A, 2A, 3A), and each sample from each lot was sampled after 0, 3, 6, 12 months.

The following tables (38A-46A) show the results for SHELF LIFE.

TABLE 38A

Lot 024A - tablets of 400 mg ion/tablet (Example 1A)

| Lot (T/t)[1] | Moisture content % (K. Fischer) | S,S % | AD[2] (%) | MTAD[3] (%) | SAMe[4] |
|---|---|---|---|---|---|
| 024 (20/0) | 0.99 | 78.1 | 0.35 | 0.81 | 410.23 |
| 024A (25/3) | 1.02 | 68.2 | 0.59 | 1.24 | 404.21 |
| 024B (25/6) | 1.05 | 64.1 | 0.78 | 1.75 | 399.32 |
| 024C (25/12) | 1.14 | 60.2 | 1.83 | 2.88 | 396.65 |

[1]Temperature (° C.)/time (months);
[2]adenosine;
[3]methylthioadenosine;
[4]SAMe sulphate p-toluene sulphonate (mg/tablet);

TABLE 39A

Lot 025A - tablets of 400 mg ion/tablet (Example 1A)

| Lot (T/t)[1] | Moisture content % (K. Fischer) | S,S % | AD[2] (%) | MTAD[3] (%) | SAMe[4] |
|---|---|---|---|---|---|
| 006 (20/0) | 1.00 | 77.3 | 0.43 | 0.79 | 411.01 |
| 025 (25/3) | 1.02 | 67.2 | 0.65 | 1.36 | 407.67 |
| 025B (25/6) | 1.15 | 65.5 | 0.87 | 1.97 | 401.87 |
| 025C (25/12) | 1.19 | 61.3 | 1.78 | 2.85 | 396.34 |

[1]Temperature (° C.)/time (months);
[2]adenosine;
[3]methylthioadenosine;
[4]SAMe sulphate p-toluene sulphonate (mg/tablet);

TABLE 40A

Lot 026A - tablets of 400 mg ion/tablet (Example 1A)

| Lot (T/t)[1] | Moisture content % (K. Fischer) | S,S % | AD[2] (%) | MTAD[3] (%) | SAMe[4] |
|---|---|---|---|---|---|
| 026 (20/0) | 1.02 | 75.7 | 0.33 | 0.85 | 410.11 |
| 006 (25/1) | 1.09 | 66.4 | 0.83 | 1.54 | 405.45 |
| 026B (25/6) | 1.23 | 63.4 | 1.08 | 2.03 | 400.43 |
| 026C (25/12) | 1.49 | 59.9 | 1.99 | 2.77 | 395.87 |

[1]Temperature (° C.)/time (months);
[2]adenosine;
[3]methylthioadenosine;
[4]SAMe sulphate p-toluene sulphonate (mg/tablet);

TABLE 41A

Lot 027A - tablets of 400 mg ion/tablet (Example 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 027 (20/0) | 0.99 | 76.7 | 0.46 | 0.83 | 409.59 | 2.12 |
| 010A (25/3) | 1.12 | 68.2 | 0.93 | 1.52 | 401.43 | 2.08 |
| 027B (25/6) | 0.98 | 62.6 | 1.59 | 2.54 | 397.53 | 2.07 |
| 027C (25/12) | 1.04 | 52.6 | 2.21 | 4.95 | 391.28 | 2.04 |

[1]Temperature (° C.)/time (months);
[2]adenosine;
[3]methylthioadenosine;
[4]SAMe sulphate p-toluene sulphonate (mg/tablet);

TABLE 42A

Lot 028A - tablets of 400 mg ion/tablet (Example 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 010 (20/0) | 0.87 | 75.8 | 0.46 | 0.83 | 409.59 | 2.12 |
| 028A (25/3) | 1.02 | 66.6 | 0.97 | 1.59 | 404.67 | 2.06 |
| 028B (25/6) | 0.99 | 61.4 | 1.74 | 2.83 | 398.93 | 2.03 |
| 028C (25/12) | 1.24 | 53.6 | 2.23 | 5.54 | 395.68 | 2.02 |

[1]Temperature (° C.)/time (months);
[2]adenosine;
[3]methylthioadenosine;
[4]SAMe sulphate p-toluene sulphonate (mg/tablet);

TABLE 43A

Lot 029A - tablets of 400 mg ion/tablet (Example 2A)

| Lot (T/t)[1] | Moisture content % (K. Fischer) | S,S % | AD[2] (%) | MTAD[3] (%) | SAMe[4] | L-melatonin mg |
|---|---|---|---|---|---|---|
| 029 (20/0) | 1.07 | 76.8 | 0.57 | 0.89 | 409.00 | 2.10 |
| 029A (25/3) | 1.06 | 67.7 | 1.42 | 1.93 | 403.28 | 2.06 |
| 029B (25/6) | 1.09 | 61.2 | 1.91 | 2.78 | 397.81 | 2.06 |
| 029C (25/12) | 1.26 | 52.6 | 2.43 | 4.76 | 393.98 | 2.04 |

[1]Temperature (° C.)/time (months);
[2]adenosine;
[3]methylthioadenosine;
[4]SAMe sulphate p-toluene sulphonate (mg/tablet);

TABLE 44A

Lot 030A - tablets of 400 mg ion/tablet (Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 030 (20/0) | 1.21 | 76.7 | 0.36 | 0.84 | 407.00 | 202.72 |
| 030A (25/3) | 1.32 | 68.7 | 1.23 | 1.43 | 402.23 | 203.33 |
| 030B (25/6) | 1.52 | 63.2 | 1.91 | 2.63 | 397.37 | 202.11 |
| 030C (25/12) | 1.43 | 53.8 | 2.53 | 4.77 | 394.88 | 201.09 |

[1]Temperature (° C.)/time (months);
[2]adenosine;
[3]methylthioadenosine;
[4]SAMe sulphate p-toluene sulphonate (mg/tablet);

TABLE 45A

Lot 031A - tablets of 400 mg ion/tablet (Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 031 (20/0) | 1.04 | 77.3 | 0.39 | 70.89 | 408.34 | 203.56 |
| 031A (25/3) | 1.11 | 66.9 | 1.41 | 1.63 | 403.83 | 202.23 |

TABLE 45A-continued

Lot 031A - tablets of 400 mg ion/tablet (Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 031B (25/6) | 1.34 | 621 | 1.98 | 2.93 | 398.44 | 201.61 |
| 031C (25/12) | 1.27 | 54.0 | 2.71 | 4.79 | 395.98 | 200.18 |

[1]Temperature (° C.)/time (months);
[2]adenosine;
[3]methylthioadenosine;
[4]SAMe sulphate p-toluene sulphonate (mg/tablet);

TABLE 46A

Lot 032A - tablets of 400 mg ion/tablet (Example 3A)

| Lot (T/t)[1] | Moisture content % (K. Fischer) | S,S % | AD[2] (%) | MTAD[3] (%) | SAMe[4] | L-theanine |
|---|---|---|---|---|---|---|
| 032 (20/0) | 1.00 | 75.3 | 0.53 | 0.92 | 406.23 | 205.52 |
| 032A (25/3) | 1.31 | 65.6 | 1.37 | 1.88 | 402.99 | 204.65 |
| 032B (25/6) | 1.30 | 57.1 | 1.79 | 2.79 | 396.47 | 203.51 |
| 032C (25/12) | 1.43 | 50.0 | 2.55 | 4.67 | 390.38 | 202.58 |

[1]Temperature (° C.)/time (months);
[2]adenosine;
[3]methylthioadenosine;
[4]SAMe sulphate p-toluene sulphonate (mg/tablet).

Results

The stability at 40° C. 75% RH (STRESS TEST) and at temperature over a long period (SHELF LIFE) for the compositions of Examples 1A, 2A and 3A (without calcium oxide) is lower than the stability for the compositions of Examples 1, 2 and 3 (with calcium oxide), valued at the same conditions (STRESS TEST and SHELF LIFE).

The invention claimed is:

1. A method for stabilizing SAMe or its salts, said method consisting of mixing calcium oxide with a powder of SAMe or its salts, and optionally adding one or more pharmaceutically acceptable excipients selected from the group consisting of calcium sulphate hemihydrate, magnesium oxide, calcium carbonate, malic acid, glutamic acid, glucono-delta lactone, hydrogenated fatty acids, anhydrous microcrystalline cellulose, precipitated silica, magnesium stearate, glycerol behenate, hydroxypropylmethylcellulose, polyvinylpyrrolidone, shellac, titanium dioxide, talc, triethyl citrate and curcumin, thereby forming a stable powder composition of SAMe or its salts.

2. The method according to claim 1, wherein SAMe or its salts is present in a quantity of between approximately 30% and approximately 90% by weight calculated in relation to the weight of the composition.

3. The method according to claim 1, wherein SAMe or its salts is present in a quantity of between approximately 50% and approximately 85% by weight calculated in relation to the weight of the composition.

4. The method according to claim 1, wherein the calcium oxide is present in a quantity which varies from approximately 1% to approximately 40% by weight with respect to the weight of the composition.

5. The method according to claim 4, wherein the calcium oxide is present in a quantity which varies from approximately 2% to approximately 20% by weight with respect to the weight of the composition.

6. The method according to claim 4, wherein one or more of the pharmaceutically acceptable excipients are added.

7. The method according to claim 1, wherein the SAMe or salt thereof is SAMe sulphate p-toluene sulphonate.

* * * * *